US006124303A

United States Patent [19]
Pamukcu et al.

[11] Patent Number: 6,124,303
[45] Date of Patent: Sep. 26, 2000

[54] METHOD FOR INHIBITING NEOPLASTIC CELLS AND RELATED CONDITIONS BY EXPOSURE TO 9-SUBSTITUTED 2-(2-N-ALOXYPHENYL) PURIN-6-ONES

[75] Inventors: Rifat Pamukcu, Spring House; Gary A. Piazza, Doylestown, both of Pa.

[73] Assignee: Cell Pathways, Inc., Horsham, Pa.

[21] Appl. No.: 09/151,937

[22] Filed: Sep. 11, 1998

[51] Int. Cl.$^7$ .................................................. A61K 31/52
[52] U.S. Cl. ............................................................ 514/262
[58] Field of Search ............................................. 514/262

[56] References Cited

U.S. PATENT DOCUMENTS

| | | | |
|---|---|---|---|
| 3,031,450 | 4/1962 | Fischer et al. | 540/600 |
| 3,161,654 | 12/1964 | Shen | 548/500 |
| 3,322,755 | 5/1967 | Roch et al. | 544/81 |
| 3,517,005 | 6/1970 | Cronin et al. | 544/293 |
| 3,594,480 | 7/1971 | Cronin et al. | 514/254 |
| 3,647,858 | 3/1972 | Hinkley et al. | 560/11 |
| 3,654,349 | 4/1972 | Shen et al. | 562/428 |
| 3,780,040 | 12/1973 | Schnettler et al. | 544/292 |
| 3,812,127 | 5/1974 | Cronin et al. | 544/363 |
| 3,819,631 | 6/1974 | Broughton et al. | 544/254 |
| 3,920,636 | 11/1975 | Takahasi et al. | 540/575 |
| 4,001,237 | 1/1977 | Partyka et al. | 544/284 |
| 4,001,238 | 1/1977 | Partyka et al. | 544/284 |
| 4,039,544 | 8/1977 | Broughton et al. | 544/254 |
| 4,060,615 | 11/1977 | Matier et al. | 514/254 |
| 4,079,057 | 3/1978 | Juby et al. | 544/287 |
| 4,098,788 | 7/1978 | Crenshaw et al. | 544/293 |
| 4,101,548 | 7/1978 | Crenshaw et al. | 544/284 |
| 4,102,885 | 7/1978 | Crenshaw et al. | 544/283 |
| 4,138,561 | 2/1979 | Crenshaw et al. | 544/284 |
| 4,146,718 | 3/1979 | Jenks et al. | 544/292 |
| 4,161,595 | 7/1979 | Kaplan et al. | 544/284 |
| 4,171,363 | 10/1979 | Crenshaw et al. | 514/254 |
| 4,208,521 | 6/1980 | Crenshaw et al. | 544/250 |
| 4,209,623 | 6/1980 | Juby | 544/319 |
| 4,423,075 | 12/1983 | Dvornik et al. | 514/569 |
| 4,460,590 | 7/1984 | Möller | 514/258 |
| 4,460,591 | 7/1984 | DeGraw et al. | 514/258 |
| 4,551,529 | 11/1985 | Kern et al. | 544/265 |
| 4,880,810 | 11/1989 | Lowe, III et al. | 514/258 |
| 4,885,301 | 12/1989 | Coates | 514/263 |
| 4,923,874 | 5/1990 | McMahon et al. | 514/258 |
| 5,073,559 | 12/1991 | Coates | 514/262 |
| 5,147,875 | 9/1992 | Coates et al. | 514/259 |
| 5,223,501 | 6/1993 | Chakravarty et al. | 514/258 |
| 5,250,535 | 10/1993 | Verheyden et al. | 514/262 |
| 5,254,571 | 10/1993 | Coates et al. | 514/344 |
| 5,358,952 | 10/1994 | Moschel et al. | 514/262 |
| 5,401,774 | 3/1995 | Pamukcu et al. | 514/569 |
| 5,439,895 | 8/1995 | Lee et al. | 514/63 |
| 5,488,055 | 1/1996 | Kumar et al. | 514/293 |
| 5,614,530 | 3/1997 | Kumar et al. | 514/293 |
| 5,614,627 | 3/1997 | Takase et al. | 544/293 |
| 5,696,159 | 12/1997 | Gross et al. | 514/468 |

FOREIGN PATENT DOCUMENTS

| | | |
|---|---|---|
| 0 347146 A2 | 12/1989 | European Pat. Off. . |
| 0 349239 A2 | 1/1990 | European Pat. Off. . |
| 0 351058 | 1/1990 | European Pat. Off. . |
| 0 352960 A2 | 1/1990 | European Pat. Off. . |
| 0 395328 A2 | 10/1990 | European Pat. Off. . |
| 0 428268 A2 | 5/1991 | European Pat. Off. . |
| 0 463756 A1 | 1/1992 | European Pat. Off. . |
| 0 485157 A2 | 5/1992 | European Pat. Off. . |
| 0 485158 A2 | 5/1992 | European Pat. Off. . |
| 0 485171 A2 | 5/1992 | European Pat. Off. . |
| 0 485172 A2 | 5/1992 | European Pat. Off. . |
| 0 485173 A2 | 5/1992 | European Pat. Off. . |
| 0 508586 A1 | 10/1992 | European Pat. Off. . |
| 0 526004 A1 | 2/1993 | European Pat. Off. . |
| 0 607439 A1 | 7/1994 | European Pat. Off. . |
| 0 722 943 A1 | 1/1996 | European Pat. Off. . |
| 0 722 944 A1 | 1/1996 | European Pat. Off. . |
| 3038166 | 5/1981 | Germany . |
| 274218 | 12/1989 | Germany . |
| 56-53659 | 5/1981 | Japan . |
| 57-167974 | 10/1982 | Japan . |
| 807826 | 1/1959 | United Kingdom . |
| 2063249 | 6/1981 | United Kingdom . |
| WO 92/03419 | 3/1992 | WIPO . |
| WO 93/07149 | 4/1993 | WIPO . |
| WO 93/12095 | 6/1993 | WIPO . |
| WO 94/05661 | 3/1994 | WIPO . |
| WO 97/03985 | 2/1997 | WIPO . |

OTHER PUBLICATIONS

Blaya, C. et al., Effect of the protein kinase inhibitors, 1–(5–isoquinolinylsulfonyl)–2–methylpiperazine H–7 and N–(2–[methylamino]ethyl)–5–isoquinoline–sulfonamide H–8 on Lewis lung carcinoma tumor progression, European Journal of Pharmacology, 354, pp. 99–104 (1998).

Chang, W. et al., Sulindac Sulfone Modulates the Expression and Cellular Localization of b–Catenin in Human Colon Carcinoma Cells, Digestive Disease Week, Apr. 1, 1999.

Earnest, D. et al., Piroxicam and Other Cyclooxygenase Inhibitors: Potential for Cancer Chemoprevention, Journal of Cellular Biochemistry, Supplement 161:156–166 (1992).

Easwaran, V. et al., The Ubiquitin–Proteasome Pathway and Serine Kinase Activity Modulate Adenomatous Polyposis Coli Protein–mediated Regulation of β–Catenin–Lymphocyte Enhancer–binding Factor Signaling, The Journal of Biological Chemistry, vol. 274, No. 23, pp. 16641–16645, Jun. 4, 1999.

Jiang, X. et al., Inhibition of calmodulin–dependent phosphodiesterase induces apoptosis in human leukemic cells, Proc. Natl. Acad. USA, vol. 83, pp. 11236–11241, Oct. 1996.

Korinek, V. et al., Constitutive Transcriptional Activation by a β–Catenin–Tcf Complex in APC$^{-/-}$ Colon Carcinoma, Science, vol. 275, pp. 1784–1786, Mar. 21, 1997.

Mahmoud, N. et al., Apc Gene Mutation is Associated with a Dominant–Negative Effect upon Intestinal Cell Migration, Cancer Research 57, pp. 5045–5050, Nov. 15, 1997.

(List continued on next page.)

*Primary Examiner*—Kathleen K. Fonda
*Attorney, Agent, or Firm*—Robert W. Stevenson

[57] ABSTRACT

A method for inhibiting neoplastic cells and related conditions by exposing them to 9-substituted 2-(2-n-alkoxyphenyl)purin-6-one compounds.

9 Claims, No Drawings

OTHER PUBLICATIONS

Mahmoud, N. et al., Genotype–Phenotype Correlation in Murine Apc Mutation: Differences in Enterocyte Migration and Response to Sulindac, Cancer Research 59, pp. 353–359, Jan. 15, 1999.

Morin, P. et al., Activation of β–Catenin–Tcf Signaling in Colon Cancer by Mutations in β–Catenin or APC, Science, vol. 275, pp. 1787–1789, Mar. 21, 1997.

Peifer, M., β–Catenin as Oncogene: The Smoking Gun, Science, vol. 275, pp. 1752–1753, Mar. 21, 1997.

Rubinfeld, B. et al., Stabilization of β–Catenin by Genetic Defects in Melanoma Cell Lines, Science, vol. 275, pp. 1790–1792, Mar. 21, 1997.

Waddel, W.R. et al., Am. J. Surgery,. vol. 157, pp. 175–179, (Jan. 1989).

Gonzaga, R.A.F. et al., The Lancet, Mar. 30, 1985, p. 751.

Waddell, W.R. et al., J. Surg. Oncology, vol. 24, pp. 83–87 (1983).

Federation Proceedings (Mar./Apr. 1972) of the Federation of American Societies for Experimental Biology abstract Nos. 2044 and 2045.

Gilman, S.C. et al., Nonsteroidal Anti–inflammatory Drugs in Cancer Therapy, (circa 1985).

Brogden, R.N. et al., Drugs, vol. 16, pp. 97–114 (1978).

Hucker, H.B. et al., Drug Metabolism & Disposition, vol. 1, No. 6, pp. 721–736 (1973).

Shen, T.Y. et al., Chemical and Biological Studies on Indomethacin, Sulindac and Their Analogs, pp. 107–178 (circa 1975).

Duggan, D.E. et al., Clin. Pharm. & Therapeutics, vol. 21, No. 3, pp. 326–335 (1976).

Duggan, D.E. et al., J. Pharm. & Exper. Therap., vol. 201, No. 1, pp. 8–13 (1977).

Glavin, G.B. et al., Toxicology and Applied Pharmacology, vol. 83, pp. 386–389 (1986).

Moorghen, M. et al., Journal of Pathology, vol. 156, pp. 341–347 (1988).

Moorghen, M. et al., Acta Histochemica, Suppl.–Band XXIX, S. 195–199 (1990).

Bjarnason et al., Gastroenterology, vol. 94, No. 4, pp. 1070–1074 (Apr. 1988).

Badrieh, Y., et al., Chem. Ber., vol. 125, pp. 667–674 (1992).

Silvola, J. et al., Effects of nonsteroidal anti–inflammatory drugs on rat gastric mucosal phosphodiesterase activity, Agents and Actions, vol. 12.4, pp. 516–520 (1982).

Curtis–Prior, P.B. et al., Cyclic Nucleotide Phosphodiesterase Activity of Human Normal and Carcinomatous Lung Tissue, The Lancet, pp. 1225–1225 Dec. 4, 1976.

Pepin, P. et al., Effects of Sulindac and Oltipraz on the tumorigenicity of 4–(methylnitrosamino)1–(3–pyridyl)–1–Butanone in A/J mouse lung, Carcinogenesis, vol. 13, No. 3, pp. 341–348 (1992).

Nicholson, C.D. et al. Differential modulation of tissue function therapeutic potential of selective inhibitors of cyclic nucleotide phosphodiesterase isoenzymes, Trends Pharmacol. Sci. (TiPS), vol. 12, pp. 19–27 (1991).

Ahn, H.S. et al., Effects of Selective Inhibitors on Cyclic Nucleotide Phosphodiesterases of Rabbit Aorta, Biochemical Pharmacology, vol. 38, No. 19, pp. 3331–3339 (1989).

Luginer, C. et al., Selective Inhibition of Cyclic Nucleotide Phosphodiesterases of Human, Bovine and Rat Aorta, Biochem. Pharmacology, vol. 35, No. 10, pp. 1743–1751 (1986).

Turner, N.C. et al., Relaxation of guinea–pig trachea by cyclic AMP phosphodiesterase inhibitors and their enhancement by sodium mitroprusside, Br. J. Pharmacol. vol. III, pp. 1047–1052 (1994).

Weishaar, R.E. et al., Multiple Molecular Forms of Cyclic Nucleotide Phosphodiesterase in Cardiac and Smooth Muscle and In Platelets, Biochem. Pharmacology, vol. 35, No. 5, pp. 787–800 (1986).

Murray, K.J. et al., Potential Use of Selective Phosphodiesterase Inhibitors in the Treatment of Asthma, New Drugs for Asthma Therapy, Birkhauser Verlag Basel, pp. 27–46 (1991).

Saeki, T. et al., Isolation of Cyclic Nucleotide Phosphodiesterase Isozymes From Pig Aorta, Biochem. Pharmacology, vol. 46, No. 5, pp. 833–839 (1993).

Turner, N.C. et al., Pulmonary effects of type V cyclic GMP specific phosphodiesterase inhibition in anaesthetized guinea–pig, Br. J. Pharmacol., vol. 111, 1198–1204 (1994).

Ferreira, S.H. et al., The molecular mechanism of action of peripheral morphone analgesia: stimulation of the cGMP system via nitric oxide release, European Journal of Pharmacology, 201 pp. 121–122 (1991).

Hidaka, H. et al., Selective Inhibitors of Three Forms of Cyclic Nucleotide Phosphodiesterase—Basic and Potential Clinical Applications, vol. 16, Advances in Cyclic Nucleotide and Protein Phosphorylation Research, pp. 245–259 (1984).

Tulshian, D. et al., Synthesis and Phosphodiesterase Actitivy of Carboxylic Acid Mimetics of Cyclic Guanosine 3",5"–Monophosphate, J. Med. Chem, vol. 36, 1210–1220 (1993).

Yasumoto, T. et al., Properties of Base–Substituted and Carboxyl–Esterified Analogues of Griseolic Acid, a Potent cAMP Phosphodiesterase Inhibitor, Biochemical Pharmacology, vol. 43, No. 10, pp. 2073,2081 (1992).

Broughton, B.J. et al., Antiallergic Activity of 2–Phenyl–8–azapruin–6–ones, Journal of Medicinal Chemistry, vol. 18, No. 11, pp. 1117–1118 (1975).

Kodama, K. et al., Effects of a novel, selective and potent phosphodiesterase type V inhibitor, E4021, on myocardial ischemia in guinea pigs, Euro. J. of Pharma. 263, pp. 93–99 (1994).

Zacharski, L. R. et al., Effect of Mopidamol on Survival in Carcinoma of the Lung and Colon: Final Report of Veterans Administration Cooperative Study No. 188, J. of the Nat'l. Cancer Inst., vol. 80, No. 2, pp. 90–96 (Mar. 1988).

Lichtner, R.B. et al., The Pyrimido–pyrimidine Derivatives RA 233 adn RX–RA 85 affect Growth and Cytoskeletal Organization of Rat Mammary Adenocarcinoma Cells, Eur. J. Cancer Clin. Oncol., vol. 23, No. 9, pp. 1269–1275 (1987).

Janik, P. et al., Inhibition of Growth of Primary and Metastatic Lewis Lung Carcinoma Cells by the Phosphodiesterase Inhibitor Isobutylmethylxanthine, Cancer Res. vol. 40, pp. 1950–1954 (Jun., 1980).

Bergstrand, Hakan et al., Effects of Antiallergic Agents, Compound 48/80, and Some Reference Inhibitors on the Activity of Partially Purified Human Lung Tissue Adenosine Cyclic 3',5'–Monophosphate and Guanosine Cyclic 3',5'–Monophosphate Phosphodiesterases, Molecular Pharmacology, 13, pp. 38–43 (1976).

Drees, Markus et al., 3',5'–Cyclic Nucleotide Phosphodiesterase in Tumor Cells as Potential Target for Tumor Growth Inhibition, Cancer Research 53, pp. 3058–3061 (Jul. 1993).

Semmler, J. et al., Xanthine derivatives: comparison between suppression of tumor necrosis factor–x production and inhibition of cAMP phosphodiesterase activity, Immunology 78, pp. 520–525 (1993).

Mehta, Rajendra et al., Structure–Activity Relationships of Brassinin in Preventing the Development of Carcinogen–Induced Mammary Lesions in Organ Culture, Anticancer Research 14: 1209–1214 (1994).

Makaryan, A.P. et al., Cyclic Nucleotides in Patients with Malignant Neoplasms of the Colon, Laboratornoe Delo, vol. 8, pp. 31–33 (1991) (English translation).

Carter et al., Chemotherapy of Cancer, $2^{nd}$ Ed., John Wiley & Sons, NY, NY, 1981, pp. 362–365.

Biddle, William et al., Antineoplastic Effect of the Pyrimido–Pyrimidine Derivative: RA 233, Pathologie Biologie, Jan., 1984, pp. 9–13.

Clarke, W.R. et al., The type III phosphodiesterase inhibitor milrinone and type V PDE inhibitor dipyridamole individually and synergistically reduce elevated pulmonary vascular resistance (Abstract Only), Pulm. Pharmacol., 7(2), pp. 81–89, (1994).

Raeburn, David et al., Effects of isoenzyme–selective inhibitors of cyclic nucleotide phosphodiesterase on microvascular leak in guinea pig airways in vivo (Abstract Only), J. Pharmacol. Exp. Ther., 267(3), pp. 1147–1151 (1993).

Marcoz, P. et al., Modulation of rat thymocyte proliferative response through the inhibition of different cyclic nucleotide phosphodiesterase isoforms by means of selective inhibitors and cGMP–elevating agents (Abstract Only), Mol. Pharmacol. 44(5) pp. 1027–1035 (1993).

Barnett, Mary S. et al., Initial biochemical and functional characterization of cyclic nucleotide phosphodiesterase isozymes in canine colonic smooth muscle (Abstract Only), J. Pharmacol. Exp. Ther., 264(2) pp. 801–812 (1993).

Molnar–Kimber, K. et al., Modulation of TNFa and IL–1B from indotoxin–stimulated monocytes by selective PDE isozyme inhibitors (Abstract Only), Agents Actions 39(Spec. Conf. Issue), C77–C79 (1993).

Giorgi, Mauro et al., Characterization of 3':5' cyclic nucleotide phosphodiesterase activities of mouse neuroblastoma N18TG2 cells (Abstract Only), FEBS Lett. 324(1) pp. 76–80 (1993).

Porter, Roderick et al., Preparation of 6–phenyl–3–(5–tetrazoly)pyridin–2(H)–one derivatives as cyclic AMP––dependent protein kinase agonists (Abstract Only), PCT Int. Appl. WO9206085 A1, (Sep. 26, 1991).

Molnar–Kimber, K. L. et al., Differential regulation of TNF–a and IL–1B production from endotoxin stimulated human monocytes by phosphodiesterase inhibitors (Abstract Only), Mediators Inflammation 1(6) pp. 411–417 (1992).

Radomski, Marek W. et al., Human Colorectal adenocarcinoma cells: differential nitric oxide synthesis determines their ability of aggregate platelets (Abstract Only), Cancer Res. 51(22) pp. 6073–6078 (1991).

Anderson, Thomas, L. G. et al., Interactions between isoprenaline, sodium nitroprusside, and isozyme–selective phosphodiesterase inhibitors on ADP–induced aggretation and cyclic Nucleotide levels in human platelets (Abstract Only), J. Cardiovasc. Pharmacol. 18(2) pp. 237–242 (1991).

Souness, John E. et al., Role of Selective cyclic GMP phosphodiesterase inhibition in the myorelaxant actions of M&B 22,943, MY–5445, vinpocetine and 1–methyl–3–isobutyl–8–(methylamino)xanthine (Abstract Only), Br. J. Pharmacol. 98(3) pp. 725–734 (1989).

Lichtner, Rosemarie B., the pyrimidopyrimidine derivatives RA233 and RX–RA85 affect cell cycle distribution of two murine tumor cell lines (Abstract Only), Eur. J. Cancer Clin. Oncol. 25(6), pp. 945–951 (1989).

Mamytbekova, A., et al., Antimetastatic effect of flurbiprofen and other platelet aggregation inhibitors (Abstract Only), Neoplasma 33(4), pp. 417–421 (1986).

Hagiwara, Masatoshi et al., Effect of 1–(3–chloroanilino)–4–phenylpthalazine (MY–5445), a specific inhibitor of cyclic CMP phosphodiesterase, on human platelet aggregation (Abstract Only), J. Pharmacol. Exp. Ther. 229(2) pp. 467–471 (1984).

METHOD FOR INHIBITING NEOPLASTIC CELLS AND RELATED CONDITIONS BY EXPOSURE TO 9-SUBSTITUTED 2-(2-N-ALOXYPHENYL) PURIN-6-ONES

TECHNICAL FIELD

This invention relates to a method for the selective inhibition of neoplastic cells, for example, for the treatment or prevention of precancerous lesions or other neoplasias in mammals.

BACKGROUND OF THE INVENTION

Each year in the United States alone, untold numbers of people develop precancerous lesions, which is a form of neoplasia, as discussed below. Such lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds that prevent or induce the remission of existing precancerous or cancerous lesions or carcinomas would greatly reduce illness and death from cancer.

For example, approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation which can be fatal. Overall, about $2.5 billion is spent annually in the United States in colon cancer treatment and prevention.

In the breast, breast cancer is often treated surgically, often by radical mastectomy with its painful and emotional aftermath. Such surgery is costly, too.

As indicated above, each lesion carries with it a chance that it will develop into a cancer. The likelihood of cancer is diminished if a precancerous lesion is removed. However, many of these patients demonstrate a propensity for developing additional lesions in the future. They must, therefore, be monitored periodically for the rest of their lives for reoccurrence.

In most cases (i.e. the cases of sporadic lesion formation, e.g. so-called common sporadic polyps), lesion removal will be effective to reduce the risk of cancer. In a small percentage of cases (i.e. cases where numerous lesions form, e.g. the so-called polyposis syndromes), removal of all or part of the effected area (e.g. the colon) is indicated. For example, the difference between common sporadic polyps and polyposis syndromes is dramatic. Common sporadic polyp cases are characterized by relatively few polyps that can usually be removed leaving the colon intact. By contrast, polyposis syndrome cases can be characterized by many (e.g. hundreds or more) of polyps—literally covering the colon in some cases—making safe removal of the polyps impossible short of surgical removal of the colon.

Because each lesion carries with it a palpable risk of cancerous development, patients who form many lesions (e.g. polyposis syndrome patients) invariably develop cancer if left untreated. Surgical removal of the colon is the conventional treatment in polyposis patients. Many polyposis patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because chemotherapy for cancer itself is often not effective and has severe side effects. Cancer chemoprevention is important for recovered cancer patients who retain a risk of cancer reoccurrence. Also, cancer prevention is important for people who have not yet had cancer, but have hereditary factors that place them at risk of developing cancer. With the development of new genetic screening technologies, it is easier to identify those patients with high-risk genetic factors, such as the potential for polyposis syndrome, who would greatly benefit from chemopreventative drugs. Therefore, finding such anti-cancer drugs that can be used for prolonged preventive use is of vital interest.

Known chemopreventative and chemotherapeutic drugs are believed to kill cancer cells by inducing apoptosis, or as sometimes referred to as "programmed cell death." Apoptosis naturally occurs in virtually all tissues of the body, and especially in self-renewing tissues such as bone marrow, gut, liver and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis play a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptosis effects, most chemotherapeutic drugs have serious side effects that prohibit their long-term use, or use in otherwise healthy individuals with precancerous lesions. These side effects, which are a result of nonspecific cytotoxicity of the drugs, include hair loss, weight loss, vomiting, immune suppression and other toxicities. For this reason, there is a need to identify new drug candidates for therapy of patients with precancerous lesions that do not have such serious side effects in humans.

In recent years, several nonsteroidal anti-inflammatory drugs ("NSAIDs"), originally developed to treat arthritis, have shown effectiveness in inhibiting and eliminating colonic polyps. Polyps virtually disappear when the patients take such drugs, particularly when the NSAID sulindac is administered. However, the prophylactic use of currently available NSAIDs, even in polyposis syndrome patients, is marked by severe side reactions that include gastrointestinal irritations and ulcerations. Once NSAID treatment is terminated due to such complications, the polyps return, particularly in polyposis syndrome patients.

Sulindac has been particularly well received among the NSAIDs for the polyp treatment. Sulindac is a sulfoxide compound that itself is believed to be inactive as an antiarthritic agent. The sulfoxide is reportedly converted by liver enzymes to the corresponding sulfide, which is acknowledged to be the active moiety as a prostaglandin synthesis inhibitor. The sulfide, however, is associated with the side effects of conventional NSAIDs. The sulfoxide is also known to be metabolized to sulfone compound that has been found to be inactive as an inhibitor of prostaglandin synthesis but active as an inhibitor of precancerous lesions.

SUMMARY OF THE INVENTION

This invention includes a method of inhibiting neoplastic cells by exposing those cells to a pharmacologically effective amount of those compounds described below. Such compounds are effective in modulating apoptosis and eliminating and inhibiting the growth of neoplasias such as precancerous lesions.

The compounds that are useful in the methods of this invention include those of Formula I below.

DETAILED DESCRIPTION OF THE INVENTION

The present invention is a method of treating a patient with neoplastic lesions by administering to a patient a pharmacologically effective amount of a pharmaceutical composition that includes a compound of Formula I.

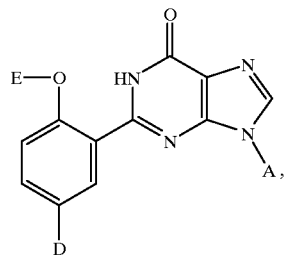

(I)

wherein A is selected from a group of the formula

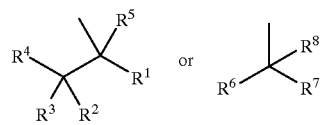

or $(CH_2)_a$—$CH_3$,

"a" is an integer from 9–15;

$R_1$ is selected from the group consisting of a straight-chain or branched alkyl group with 2 to 10 carbon atoms, which is optionally substituted by phenyl, which in turn may be substituted by halogen, nitro, cyano, straight-chain or branched alkyl with up to 6 carbon atoms, or by a group with the formula —$SO_2NR^9R_{10}$;

wherein $R_9$ and $R_{10}$ are the same or different, and are each is independently selected from the group consisting of hydrogen, phenyl, or straight-chain or branched alkyl with up to 6 carbon atoms, which is optionally substituted by hydroxy; or together with the nitrogen atom $R_9$ and $R_{10}$ form a 5- to 6-membered saturated heterocyclic ring with up to 2 other hetero atoms from the group consisting of S, N, and/or O, which is also optionally substituted through a free N function by a straight-chain or branched alkyl with up to 6 carbon atoms, which in turn may be substituted by hydroxy, and/or is alkyl optionally substituted by a group with the formula —$NR_{11}R_{12}$;

$R^2$ is selected from the group consisting of hydrogen, azido, straight-chain or branched alkyl with up to 6 carbon atoms or a group with the formula —$OR_{13}$, —O—$SO_2R_{14}$, or —$NR_{15}R_{16}$;

wherein $R_{13}$ is selected from the group consisting of hydrogen, a hydroxy-protecting group, straight-chain or branched alkyl with up to 6 carbon atoms, benzoyl or straight-chain or branched alkyl with up to 6 carbon atoms, which is optionally substituted by carboxy or straight-chain or branched alkoxycarbonyl with up to 6 carbon atoms, or by a group with the formula —CO—$NR_{17}R_{18}$, wherein $R_{17}$ and $R_{18}$ are the same or different and are selected from the group consisting of hydrogen or straight-chain or branched alkyl with up to 4 carbon atoms, $R_{14}$ is selected from the group consisting of straight-chain or branched alkyl with up to 4 carbon atoms or phenyl, $R_{15}$ and $R_{16}$ are the same or different and are selected from a group consisting of hydrogen, an amine-protecting group, straight-chain or branched alkyl or acyl, each with up to 6 carbon atoms, formyl, benzoyl, or a group with the formula —$SO_2R_{19}$, wherein $R_{19}$ has the meaning given above for $R_{14}$ and is the same as or different from it, $R_3$ is hydrogen, or $R^2$ and $R^3$ together form a group of the formula =O or =N—$OR_{20}$;

wherein $R_{20}$ is selected from a group consisting of hydrogen or straight-chain or branched alkyl with up to 6 carbon atoms, which is optionally substituted by phenyl or by a group with the formula —NR$_{21}$R$_{22}$;

wherein R$_{21}$ and R$_{22}$ are the same or different and are selected from a group consisting of hydrogen, phenyl, or straight-chain or branched alkyl with up to 6 carbon atoms;

R$_4$ is selected from a group consisting of hydrogen or straight-chain or branched alkyl with up to 4 carbon atoms;

R$_5$ and R$_8$ are the same or different and stand for hydrogen or straight-chain or branched alkyl with up to 3 carbon atoms;

R$_6$ is selected from a group consisting of hydrogen or straight-chain or branched alkyl with up to 5 carbon atoms, which is optionally substituted by hydroxy;

R$_7$ is selected from the group consisting of straight-chain or branched alkyl with 2 to 8 carbon atoms, which is substituted by a group with the formula —NR$_{23}$R$_{24}$;

wherein R$_{23}$ and R$_{24}$ are the same or different and stand for hydrogen or straight-chain or branched alkyl with up to 5 carbon atoms, which is optionally substituted by hydroxy, or is optionally substituted by phenyl, which in turn is substituted by the group with the formula —SO$_2$—NR$_{25}$R$_{26}$;

wherein R$_{25}$ and R$_{26}$ have the meanings given above for R$_9$ and R$_{10}$;

D is selected from a group consisting of hydrogen or for a group with the formula —SO$_2$—NR$_{27}$R$_{28}$;

wherein R$_{27}$ and R$_{28}$ are the same or different and have the meanings given above for R$_9$ and R$_{10}$, and are the same as them or different from them; and E is selected from a group consisting of straight-chain or branched alkyl with up to 8 carbon atoms, and their tautomers and salts.

The compounds useful in the practice of this invention can also be in the form of salts. Physiologically acceptable salts are preferred. Physiologically acceptable salts can be salts of the compounds pursuant to the invention with inorganic or organic acids. Preferred salts are those with inorganic acids, for example, hydrochloric acid, hydrobromic acid, phosphoric acid, or sulfuric acid, or salts with organic carboxylic acids or sulfonic acids, for example acetic acid, maleic acid, fumaric acid, malic acid, citric acid, tartaric acid, lactic acid, benzoic acid, or methanesulfonic acid, ethanesulfonic acid, benzenesulfonic acid, toluenesulfonic acid, or naphthalenedisulfonic acid.

The compounds of Formula I can occur in various stereochemical forms, which have the nature either of image and mirror image (enantiomers) or which are not mirror images of one another (diastereoisomers). The methods of this invention can be practiced with both the antipodes and to the racemic forms, and to mixtures of diastereoisomers. The racemic forms can be separated, as can the diastereoisomers, into their stereoisomerically pure components, by known methods.

A 5- to 6-membered saturated heterocyclic ring bonded through the nitrogen atom, which also may contain up to 2 oxygen, sulfur, and/or nitrogen atoms as hetero atoms, generally are selected from a group consisting of piperidyl, morpholinyl, piperazinyl, or pyrrolidinyl. Piperidyl and morpholinyl are especially preferred.

Hydroxy-protecting groups generally refer to protective group selected from a group consisting of: trimethylsilyl, triethylsilyl, triisopropylsilyl, t-butyldimethylsilyl, triphenylsilyl, or benzyl. Trimethylsilyl, t-butyldimethylsilyl, or benzyl are preferred.

Amine-protecting groups in the context of the invention are the usual amine-protecting groups used in peptide chemistry. Preferred representatives of them are: benzyloxycarbonyl, methoxycarbonyl, ethoxycarbonyl, propoxycarbonyl, isopropoxycarbonyl, butoxycarbonyl, isobutoxycarbonyl, t-butoxycarbonyl, formyl, or acetyl.

Preferred compounds of Formula I for the practice of this invention are those wherein "A" is selected from a group consisting of moieties of the formula

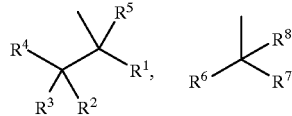

or (CH$_2$)$_a$—CH$_3$, wherein "a" is an integer from 9–13,

R$_1$ is selected from a group consisting of straight-chain or branched alkyl group with 2 to 8 carbon atoms, which is optionally substituted by phenyl, which in turn may be substituted by fluorine, chlorine, bromine, nitro, cyano, straight-chain or branched alkyl with up to 4 carbon atoms, or by a group with the formula —SO$_2$NR$_{11}$R$_{12}$;

wherein R$_9$ and R$_{10}$ are the same or different, and are selected from a group consisting of hydrogen, phenyl, or straight-chain or branched alkyl with up to 5 carbon atoms, which is optionally substituted by hydroxy, or together with the nitrogen atom they form a morpholinyl, pyrrolidinyl, piperidinyl, or piperazinyl ring, which is also optionally substituted through a free NH function by straight-chain or branched alkyl with up to 3 carbon atoms, which in turn may be substituted by hydroxy, and/or is alkyl optionally substituted by a group with the formula —NR$_{11}$R$_{12}$;

wherein R$_{11}$R$_{12}$ have the meanings given above for R$_9$ and R$_{10}$ and are the same as them or different from them;

R$_2$ is selected from a group consisting of hydrogen, azido, straight-chain or branched alkyl with up to 4 carbon atoms or a group with the formula —OR$_{13}$, —O—SO$_2$R$_{14}$, or —NR$_{15}$R$_{16}$;

wherein R$_{13}$ is selected from a group consisting of hydrogen, benzyl, straight-chain or branched acyl with up to 4 carbon atoms, benzoyl or straight-chain or branched alkyl with up to 4 carbon atoms, which is optionally substituted by carboxy or straight-chain or branched alkoxycarbonyl with up to 4 carbon atoms, or by a group with the formula —CO—NR$_{17}$R$_{18}$;

wherein R$_{17}$R$_{18}$ are the same or different and are selected from a group consisting of hydrogen or straight-chain or branched alkyl with up to 3 carbon atoms;

R$_{14}$ is selected from a group consisting of straight-chain or branched alkyl with up to 3 carbon atoms or phenyl;

R$_{15}$ and R$_{16}$ are the same or different and are selected from a group consisting of hydrogen, t-butoxycarbonyl, benzyloxycarbonyl, or straight-chain or branched alkyl or acyl, each with up to 4 carbon atoms, formyl, benzoyl, or a group with the formula —SO$_2$R$_{19}$;

wherein R$_{19}$ has the meaning given above for R$_{14}$ and is the same as or different from it;

R$_3$ is selected from a group consisting of hydrogen, or R$_2$ and R$_3$ together form a group of the formula =O or =N—OR$_{20}$, wherein R$_{20}$ is selected from a group consisting of hydrogen or straight-chain or branched alkyl with up to 4 carbon atoms, which is optionally substituted by phenyl or by a group with the formula —NR$_{21}$R$_{22}$;

wherein R$_{21}$ and R$_{22}$ are the same or different and stand for hydrogen, phenyl, or straight-chain or branched alkyl with up to 4 carbon atoms;

R$_4$ is selected from a group consisting of hydrogen or straight-chain or branched alkyl with up to 3 carbon atoms;

$R_5$ and $R_8$ are the same or different and stand for hydrogen or methyl;

$R_6$ is selected from the group consisting of hydrogen or straight-chain or branched alkyl with up to 3 carbon atoms, which is optionally substituted by hydroxy;

$R_7$ is selected from the group consisting of straight-chain or branched alkyl with 2 to 6 carbon atoms, which is substituted by a group with the formula —$NR_{23}R_{24}$;

wherein $R_{23}$ and $R_{24}$ are the same or different and are selected from the group consisting of hydrogen or straight-chain or branched alkyl with up to 4 carbon atoms, which is optionally substituted by hydroxy, or is optionally substituted by phenyl, which in turn is substituted by a group with the formula —$SO_2$—$NR_{25}R_{26}$;

wherein $R_{25}$ and $R_{26}$ are the same or different and have the meanings given above for $R_9$ and $R_{10}$;

D is selected from a group consisting of hydrogen or for a group with the formula —$SO_2$—$NR_{27}R_{28}$;

wherein $R_{27}$ and $R_{28}$ are the same or different and have the meanings given above for $R_9$ and $R_{10}$, and are the same as them or different from them; and E is selected from a group consisting of straight-chain or branched alkyl with up to 6 carbon atoms, and their tautomers and salts.

In the practice of this invention, especially preferred are compounds of Formula I in which A is selected from a group with the formula

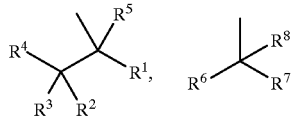

or $(CH_2)_a$—$CH_3$;

wherein "a" is an integer from 9–12;

$R_1$ is selected from a group consisting of a straight-chain or branched alkyl group with 2 to 7 carbon atoms, which is optionally substituted by phenyl, which in turn may be substituted by fluorine, chlorine, bromine, nitro, cyano, straight-chain or branched alkyl with up to 3 carbon atoms, or by a group with the formula —$SO_2NR_9R_{10}$;

wherein $R_9$ and $R_{10}$ are the same or different, and are selected from a group consisting of hydrogen, phenyl, or straight-chain or branched alkyl with up to 4 carbon atoms, which is optionally substituted by hydroxy, or together with the nitrogen atom they form a morpholinyl, pyrrolidinyl, piperidinyl, or piperazinyl ring, which is also optionally substituted through a free NH function by straight-chain or branched alkyl with up to 3 carbon atoms, which in turn may be substituted by hydroxy, and/or is alkyl optionally substituted by a group with the formula —$NR_{11}R_{12}$;

wherein $R_{11}$ and $R_{12}$ have the meanings given above for $R^9$ and $R_{10}$ and are the same as them or different from them;

$R_2$ is selected from a group consisting of hydrogen, azido, straight-chain or branched alkyl with up to 3 carbon atoms or a group with the formula —$OR_{13}$, —O—$SO_2R_{14}$, or —$NR_{15}R_{16}$;

wherein $R_{13}$ is selected from a group consisting of hydrogen, straight-chain or branched acyl with up to 3 carbon atoms, benzoyl or straight-chain or branched alkyl with up to 3 carbon atoms, which is optionally substituted by carboxy or straight-chain or branched alkoxycarbonyl with up to 3 carbon atoms, or by a group with the formula —CO—$NR_{17}R_{18}$;

wherein $R_{17}$ and $R_{18}$ are the same or different and are selected from the group consisting of hydrogen and lower alkyl;

$R_{14}$ is selected from a group consisting of straight-chain or branched alkyl with up to 3 carbon atoms or phenyl;

$R_{15}$ and $R_{16}$ are the same or different and are selected from a group consisting of hydrogen, t-butoxycarbonyl, straight-chain or branched alkyl or acyl, each with up to 3 carbon atoms, formyl, benzoyl, or a group with the formula —$SO2R_{19}$, wherein $R_{19}$ has the meaning given above for $R_{14}$ and is the same as or different from it;

$R_3$ is hydrogen, or $R_2$ and $R_3$ together form a group with the formula =O or =N—$OR_{20}$;

wherein $R_{20}$ is selected from a group consisting of hydrogen or straight-chain or branched alkyl with up to 4 carbon atoms, which is optionally substituted by phenyl or by a group with the formula —$NR_{21}R_{22}$;

wherein $R_{21}$ and $R_{22}$ are the same or different and are selected from a group consisting of hydrogen, phenyl, or straight-chain or branched alkyl with up to 3 carbon atoms;

$R_4$ is selected from a group consisting of hydrogen or straight-chain or branched alkyl with up to 3 carbon atoms;

$R_5$ and $R_8$ are the same or different and are selected from a group consisting of hydrogen or methyl;

$R_6$ is selected from a group consisting of hydrogen or straight-chain or branched alkyl with up to 3 carbon atoms, which is optionally substituted by hydroxy;

$R_7$ is selected from a group consisting of straight-chain or branched alkyl with 2 to 6 carbon atoms, which is substituted by a group with the formula —$NR_{23}R_{24}$;

wherein $R_{23}$ and $R_{24}$ are the same or different and are selected from the groups consisting of hydrogen or a straight-chain or branched alkyl with up to 3 carbon atoms, which is optionally substituted by hydroxy, or is optionally substituted by phenyl, which in turn is substituted by the group with the formula —$SO_2$—$NR_{25}R_{26}$, wherein $R_{25}$ and $R_{26}$ have the meanings given above for $R_9$ and $R_{10}$;

D is selected from a group consisting of hydrogen or for a group with the formula —$SO_2$—$NR_{27}R_{28}$;

wherein $R_{27}$ and $R_{28}$ are the same or different and have the meanings given above for $R_9$ and $R_{10}$, and are the same as them or different from them; and E is selected from a group consisting of straight-chain or branched alkyl with up to 5 carbon atoms; and their tautomers and salts.

Preferably, such compositions are administered without therapeutic amounts of an NSAID.

The present invention is also a method of treating individuals with neoplastic lesions by administering a pharmacologically effective amount of an enterically coated pharmaceutical composition that includes compounds of this invention.

Also, the present invention is a method of inhibiting the growth of neoplastic cells by exposing the cells to an effective amount of compounds of Formula I, wherein $R_1$ etc. are defined as above.

In still another form, the invention is a method of inducing apoptosis in human cells by exposing those cells to an effective amount of compounds of Formula I, wherein $R_1$ etc. are defined as above where such cells are sensitive to these compounds.

Additionally, in yet another form, the invention is a method of treating a patient having a disease which would benefit from regulation of apoptosis by treating the patient with an effective amount of compounds of Formula I, wherein $R_1$ etc. are defined as above. The regulation of apoptosis is believed to play an important role in diseases associated with abnormalities of cellular growth patterns such as benign prostatic hyperplasia, neurodegenerative diseases such as Parkinson's disease, autoimmune diseases including multiple sclerosis and rheumatoid arthritis, infectious diseases such as AIDS, and other diseases, as well.

As used herein, the term "precancerous lesion" includes syndromes represented by abnormal neoplastic, including dysplastic, changes of tissue. Examples include dysplasic growths in colonic, breast, bladder or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), esophagus, prostatic dysplasia, bronchial dysplasia, breast, bladder and/or skin and related conditions (e.g., actinic keratosis), whether the lesions are clinically identifiable or not.

As used herein, the term "carcinomas" refers to lesions that are cancerous. Examples include malignant melanomas, breast cancer, prostate cancer and colon cancer.

As used herein, the term "neoplasm" refers to both precancerous and cancerous lesions and hyperplasia.

Compounds useful in the practice of this invention may be formulated into pharmaceutical compositions together with pharmaceutically acceptable carriers for oral administration in solid or liquid form, or for rectal or topical administration, although carriers for oral and parenteral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g., pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for topical administration include DMSO, alcohol or propylene glycol and the like that can be employed with patches or other liquid-retaining material to hold the medicament in place on the skin so that the medicament will not dry out.

Pharmaceutically acceptable carriers for rectal administration are preferably suppositories that may contain, in addition to the compounds of this invention excipients such as cocoa butter or a suppository wax, or gel.

When the present invention is used as a medicine for such diseases, it is administered by oral administration or parenteral administration. The dose thereof varies depending upon the extent of symptom; the age, sex, weight and drug sensitivity of a patient; the method, timing and interval of administration; the type of pharmaceutical preparation; the type of a medicine to be administered together therewith; the type of an active ingredient and so forth.

In oral or injectible administration, the total daily dose should generally about 0.2 to 150 mg. administered in 1 to 3 doses a day.

A method for making compounds useful in the practice of this invention is described in EP 722,943 and can be illustrated by the following schematic diagrams:

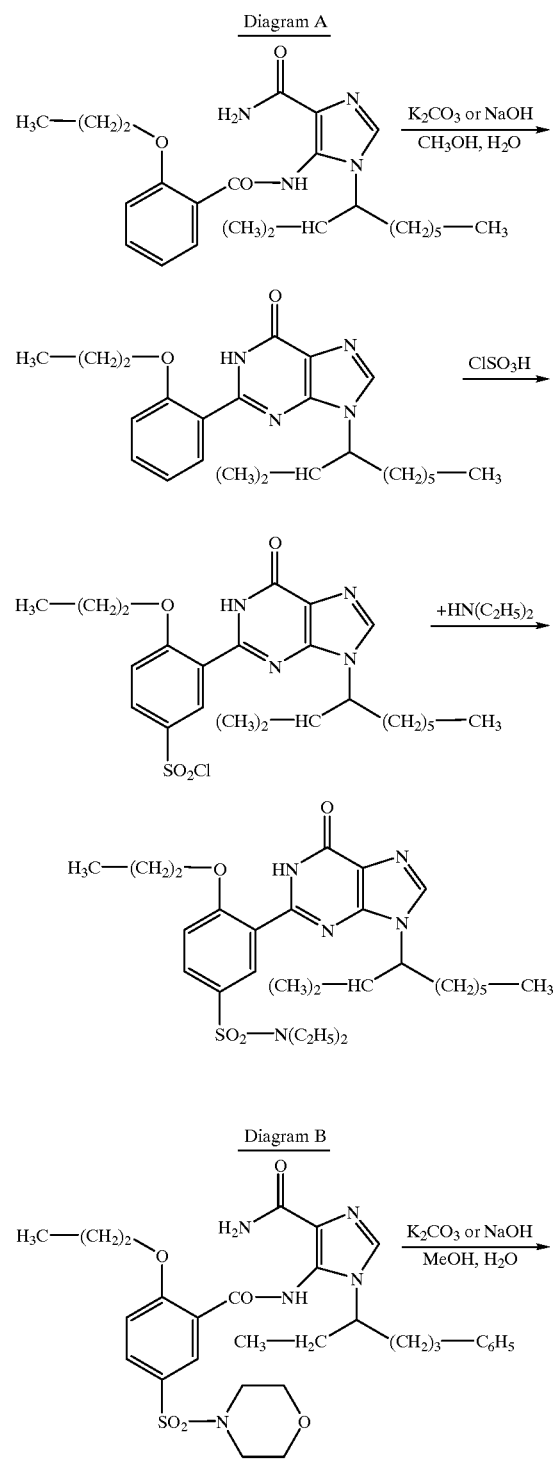

-continued

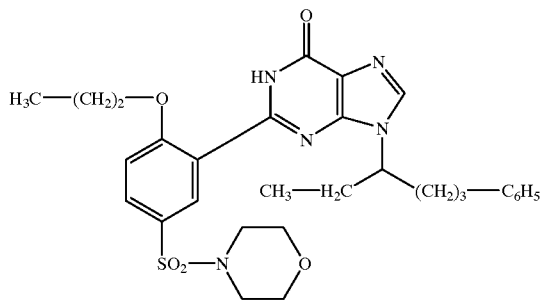

Inert organic solvents that do not change under the reaction conditions are suitable for the method. Preferred inorganic solvents are diethyl ether, dioxane, tetrahydrofuran, ethylene glycol mono- or dimethyl ether, ethyl acetate, toluene, acetonitrile, hexamethylphosphoric triamide, pyridine, and acetone. It is also possible to use mixtures of such solvents. Tetrahydrofuran, toluene, or pyridine are especially preferred.

Suitable solvents for the cyclization are the usual organic solvents. Preferred organic solvents are alcohols such as methanol, ethanol, propanol, or butanol, or ethers, such as tetrahydrofuran or dioxane, or dimethylformamide or dimethyl sulfoxide. It is especially preferred to use alcohols such as methanol, ethanol, propanol, or isopropanol. It is likewise possible to use mixtures of such solvents.

Suitable bases for the cyclization are the usual inorganic bases. Preferred examples of them are alkali metal hydroxides or alkaline earth hydroxides, for example sodium hydroxide, potassium hydroxide, or barium hydroxide, or alkali metal carbonates such as sodium or potassium carbonate, or sodium bicarbonate, or alkali metal alkoxides such as sodium ethoxide, sodium methoxide, potassium methoxide, potassium ethoxide, or potassium t-butoxide. Especially preferred are potassium carbonate and sodium hydroxide.

When carrying out the cyclization, the base is used in an amount of 2 to 6 moles, preferably from 3 to 5 moles, per mole of the compounds of Formula (II).

The cyclization is carried out in the temperature range of 0° C. to 160° C., preferably at the boiling point of the particular solvent.

The cyclization is carried out at atmospheric pressure. However, it is also possible to carry out the process at elevated or reduced pressure (for example, in the range from 0.5 to 5 bar).

The chlorosulfonation is performed either without solvent or in the presence of one of the inert solvents listed above.

The sulfonamides are usually prepared in one of the solvents listed above, preferably in tetrahydrofuran or dichloromethane.

The chlorosulfonation and amidation are usually performed in the temperature range of −20° C. to +80° C., preferably from −10° C. to +30° C., and at atmospheric pressure. Besides the bases listed above, preferable bases suitable for this in some cases are triethylamine and/or dimethylaminopyridine, DBU, or DABCO. It is likewise possible to use an excess of the amine that is used.

The base is used in an amount of 0.5 mole to 10 moles, preferably from 1 mole to 3 moles per mole of the corresponding chlorosulfonic acid.

The alkylation is usually carried out with alkylating agents, for example such as $(C_{1-10})$-alkyl halides, sulfuric acid esters, or substituted or unsubstituted $(C_1–C_{10})$-dialkyl sulfonates or $(C_1–C_{10})$-diaryl sulfonates, preferably methyl iodide or dimethyl sulfate.

Solvents suitable for the alkylation are also the usual organic solvents that do not change under the reaction conditions. Preferred examples of these are ethers such as diethyl ether, dioxane, tetrahydrofuran, ethylene glycol dimethyl ether, or hydrocarbons such as benzene, toluene, xylene, hexane, cyclohexane, or petroleum fractions, or halogenated hydrocarbons such as dichloromethane, trichloromethane, tetrachloromethane, dichloroethylene, trichloroethylene, or chlorobenzene, or ethyl acetate, dimethylformamide, hexamethylphosphoramide, acetonitrile, or acetone. It is likewise possible to use mixtures of the solvents mentioned. Dichloromethane is preferred.

The alkylation is carried out in the solvents listed above at temperatures of 0° C. to +150° C., preferably between room temperature and +100° C., at atmospheric pressure.

The amine-protecting groups are split off by known methods under acidic or basic conditions, or reductively by catalytic hydrogenation, for example with Pd/C in organic solvents such as ethers, e.g. tetrahydrofuran or dioxane, or alcohols, for example methanol, ethanol, or isopropanol.

The hydroxy-protecting groups are split off from the corresponding esters by the usual hydrolytic methods.

The reaction with alkylsulfonyl chlorides occurs, starting from the corresponding free hydroxy compounds, in one of the solvents listed above and one of the bases, preferably with dichloromethane and triethylamine, in a temperature range from −20° C. to +20° C., preferably at 0° C. and atmospheric pressure.

The azide group is introduced by reacting the corresponding alkylsulfonyloxy-substituted compounds with sodium azide in one of the solvents listed above, preferably dimethylformamide, in a temperature range of 50° C. to +120° C., preferably at 100° C. and atmospheric pressure.

The azido-substituted compounds are reduced to the corresponding free amines by hydrogenation in one of the alcohols listed above, preferably methanol, with hydrogen in the presence of a palladium catalyst, preferably Pd/C, in a temperature range of 0° C. to +50° C., preferably at 25° C. The hydrogenation is usually carried out at atmospheric pressure.

The acylations are carried out from the corresponding free amino or hydroxy compounds in one of the solvents listed above, preferably dichloromethane, and in the presence of one of the bases listed above, preferably triethylamine with addition of dimethylaminopyridine (DMAP), in a temperature range of 0° C. to +80° C., preferably at +20° C. to +40° C., at atmospheric pressure.

The ketones are prepared by known methods (Swern Oxidation) from the corresponding hydroxy compounds.

The oximes are usually made by reacting the corresponding ketone with hydroxylamines in one of the alcohols listed above, preferably methanol, at reflux temperature and atmospheric pressure.

The enantiomerically pure compounds are available by the usual methods, for example by chromatography of the racemic compounds of Formula I on chiral phases.

Some of the compounds of general Formula (II) can be prepared by reacting compounds with the general Formula III

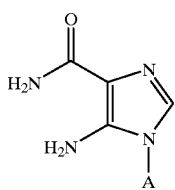

(III)

in which A has the meaning given above with 2-n-alkoxybenzoyl chlorides of the general formula (IV)

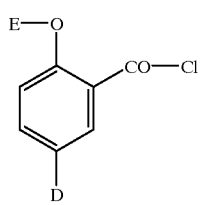

(IV)

in which D and E have the meanings given above, in inert solvents and in the presence of a base.

The solvents listed above are suitable as solvents, with toluene and tetrahydrofuran being preferred.

Suitable as bases in general are alkali metal hydrides or alkoxides, for example such as sodium hydride or potassium t-butoxide, or cyclic amines, for example such as piperidine, pyridine, dimethylaminopyridine, or $C_1$–$C_4$-alkylamines, for example such as triethylamine. Sodium hydride, pyridine, and dimethylaminopyridine are preferred.

The base is generally used in an amount of 1 mole to 4 moles, preferably from 1.2 moles to 3 moles, per mole of the compounds of general Formula (III).

The reaction temperature can be varied within a broad range. The preferred operating temperature is in the range of –20° C. to 200° C., most preferably from 0° C. to 25° C.

In a variant, the reaction is carried out in pyridine to which a catalytic amount of DMAP has been added. Toluene can also be added.

The compounds of Formula IV are reportedly known.

Most of the compounds of general Formula (III) can be prepared, for example, by reacting 2-amino-2-cyanoacetamide of Formula V.

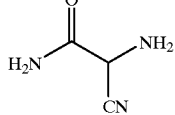

(V)

with compounds of Formula VI

(VI)

in which A has the meaning given above, in inert solvents in the presence of triethyl orthoformate.

Solvents suitable for the individual steps of the process are the usual organic solvents that do not change under the reaction conditions. Preferred examples of them are ethers such as diethyl ether, dioxane, tetrahydrofuran, ethylene glycol dimethyl ether, or hydrocarbons such as benzene, toluene, xylene, hexane, cyclohexane, or petroleum fractions, or halogenated hydrocarbons such as dichloromethane, trichloromethane, tetrachloromethane, dichloroethylene, trichloroethylene, or chlorobenzene, or ethyl acetate, dimethylformamide, hexamethylphosphoramide, acetonitrile, acetone, or dimethoxyethane. It is likewise possible to use mixtures of the solvents mentioned. Acetonitrile is especially preferred.

The process of the invention is usually carried out in a temperature range of 0° C. to +180° C., preferably from +30° C. to +150° C.

The steps of the process pursuant to the invention are usually carried out at atmospheric pressure. However, it is also possible to operate at elevated pressure or reduced pressure (for example in a range from 0.5 to 5 bar).

The compound of Formula V is reportedly known [see. Logermann, G. Shaw, Chemistry and Industry, 1980 (13), 541–542].

Some of the amines of Formula VI are reportedly known and in any event can be prepared by known methods [see, e.g., L. R. Krepski et al., Synthesis, 1986, 301–303].

The foregoing may be better understood from the following examples from the aforesaid European patent application that are presented for purposes illustrating compounds useful in practicing this invention and are not intended to limit the scope of the invention.

Starting Materials

There are two general procedures for preparing 1-substituted 5-(2-n-alkoxybenzoylamino)imidazole-4-carboxamides starting materials of Formula IV that are designated Methods A and B below.

Method A 10 mmoles of 1-substituted 5-aminoimidazole-4-carboxamide and 15 mmoles of NaH (if one of the aforementioned groups $R_1$, $R_2$, $R_3$, $R_4$, $R_5$, $R_6$ $R_7$, or $R_8$ contains a hydroxy group, 30 mmoles of NaH is used) in 50 ml of absolute THF are stirred for 3 hours at 20° C. (refluxing for up to 12 hours in the case of sparingly soluble imidazoles). 10 mmoles of 2-n-alkoxybenzoyl chloride (or 20 mmoles if a hydroxy group is present) in 25 ml of absolute THF is added dropwise at 20° C., and the mixture is stirred overnight at room temperature. The solvent is evaporated, and the residue is taken up in ethyl acetate and extracted with water. The organic phase is dried over $Na_2SO_4$, evaporated, and the residue is purified by recrystallization or flash chromatography.

If the 5-aminoimidazole-4-carboxamide contains a free hydroxy group in the groups $R_1$, $R_2$, $R_3$, $R_4$, $R_5$, $R_6$, $R_7$, or $R_8$, it is in the form of an ester of a 2-n-alkoxybenzoic acid, which can be saponified by known methods (1 N NaOH, $CH_3OH$). However, it is also possible to cyclize the esters to the purinones directly with NaOH as the base, with the ester also being hydrolyzed.

Method B 10 mmoles of 1-substituted 5-aminoimidazole-4-carboxamide and 50 mg of DMAP are mixed in 20 ml of dry pyridine at room temperature. To this is added dropwise a solution of 10 mmoles of n-alkoxybenzoyl chloride in 10 ml of absolute toluene, and the mixture is stirred at room temperature until the reaction is complete according to TLC (30 minutes to 16 hours). The precipitate is filtered off, and the solvent is evaporated in a rotary evaporator under vacuum. The residue is taken up in 30 ml of methylene chloride and washed with 30 ml of 1 N HCl and 30 ml of $H_2O$. After drying over $Na_2SO_4$, the solvent is evaporated, and the residue is purified by flash chromatography or recrystallization.

The 1-substituted 5-(2-n-alkoxybenzoylamino)imidazole-5-carboxamides listed in Table I are prepared according to the methods above:

TABLE I
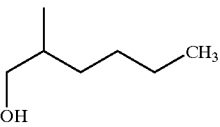
| 1) Example No. | A. | D | 2) Yield (%) | 3) M.p.(° C.)/R$_f$ |
|---|---|---|---|---|
| I | 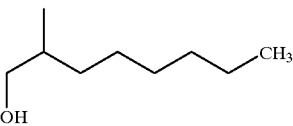 | H | 41 | |
| II | 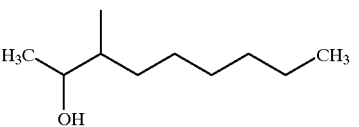 | H | 38 | |
| III | 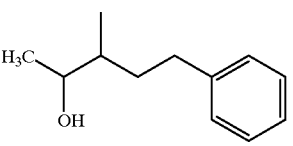 | H | 52 | |
| IV | 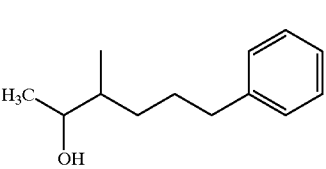 | H | 57 | |
| V | 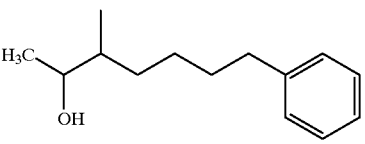 | H | 11 | 104 (Ether) |
| VI | 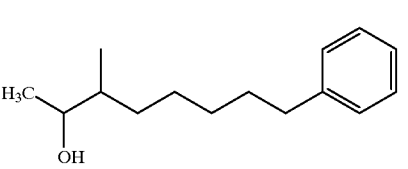 | H | 12 | |
| VII | 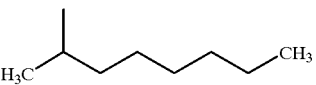 | H | 41 | |
| VIII | | H | 30 | |

TABLE I-continued
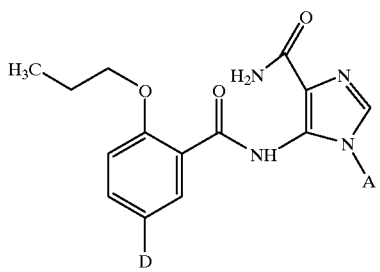
| 1) Example No. | A. | D | 2) Yield (%) | 3) M.p.(° C.)/R_f |
|---|---|---|---|---|
| IX | H₃C−CH(CH₃)−(CH₂)₅−CH₃ (4-methyl) | H | 26.6 | |
| X | H₃C−CH(CH₃)−CH(CH₃)−(CH₂)₄−CH₃ | H | 46 | |
| XI | H₃C−CH(CH₃)−(CH₂)₂−C₆H₅ | H | 30 | |
| XII | H₃C−CH₂−CH(CH₃)−(CH₂)₂−C₆H₅ | H | 50 | |
| XIII | H₃C−CH(CH₃)−CH(CH₃)−(CH₂)₂−C₆H₅ | H | 26 | |
| XIV | CH₃CH₂CH₂−N(C₂H₅)₂ | H | 27 | |
| XV | CH(CH₃)−(CH₂)₁₁−CH₃ | H | 41 | |
| XVI | CH₂CH₂CH₂CH₂−N(CH₃)−CH₂CH₂OH | H | 8 | |
| XVII | H₃C−CH₂−CH(CH₃)−(CH₂)₂−C₆H₅ | −O₂S−N(morpholine) | 27 | |

TABLE I-continued

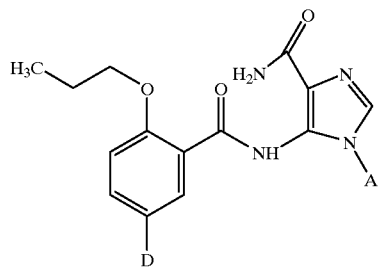

| 1) Example No. | A. | D | 2) Yield (%) | 3) M.p.(° C.)/$R_f$ |
|---|---|---|---|---|
| XVIII | H₃C-CH(CH₃)-CH₂-CH₂-CH₂-C₆H₅ (branched with CH₃) | —O₂S—N(morpholine) | 33 | |
| XIX | H₃C-CH(OH)-CH(CH₃)-CH₂-CH₂-C₆H₅ | —O₂S—N(morpholine) | 53 | |
| XX | H₃C-CH(CH₃)-CH₂-CH₂-CH₂-C₆H₅ | —O₂S—N(morpholine) | 38 | |

1) Example No.
2) Yield (%)
3) M.p.(° C.)/$R_f$

General Procedures

General procedures for preparing 9-substituted 2-(2-n-alkoxyphenyl)purin-6-ones of Formula I are set forth below.

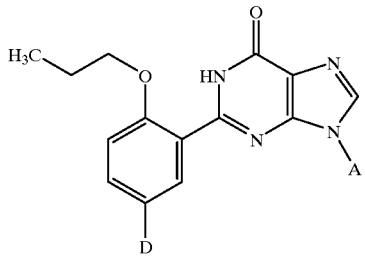

10 mmoles of the 1-substituted 5-(2-n-alkoxybenzoylamino)imidazole-4-carboxamide (IV) and 40 mmoles of $K_2CO_3$ in a mixture of 100 ml of ethanol and 50 ml of water are refluxed overnight. The solvent is distilled off under vacuum, and the residue is taken up in ethyl acetate, and extracted twice with water. After drying the organic phase over sodium sulfate, the solvent is evaporated and the residue is purified by recrystallization or flash chromatography.

The compounds listed in Table II are prepared according to the methods described immediately above.

TABLE II
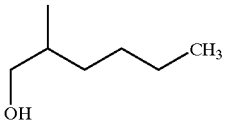
| 1) Example No. | A. | D | 2) Yield (%) | 3) M.p.(° C.)/R$_f$ |
|---|---|---|---|---|
| 1 | 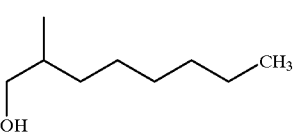 | H | 63 | 186 |
| 2 | 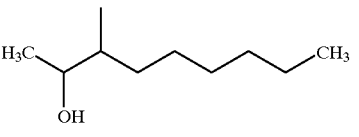 | H | 87 | 0.33 a) |
| 3 | 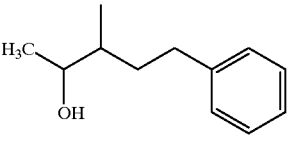 | H | 67 | 113 |
| 4 | 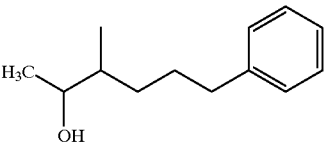 | H | 39 | 82 |
| 5 | 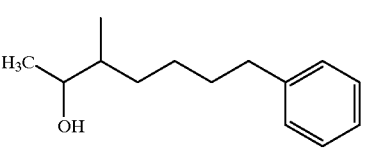 | H | 51 | 104 |
| 6 | 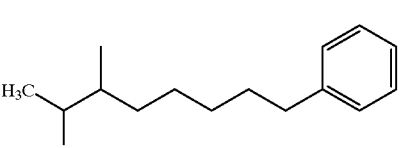 | H | 27 | 68 |
| 7 | 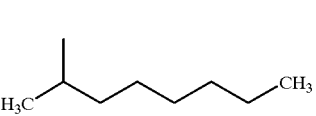 | H | 31 | 91 |
| 8 |  | H | 75 | 0.58 a) |

TABLE II-continued
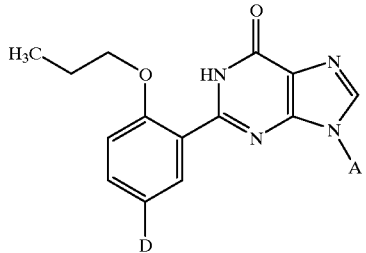
| 1)<br>Example No. | A. | D | 2)<br>Yield (%) | 3)<br>M.p.(° C.)/R$_f$ |
|---|---|---|---|---|
| 9 | 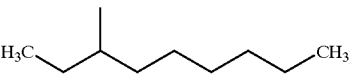 | H | 54 | 0.6 a) |
| 10 | 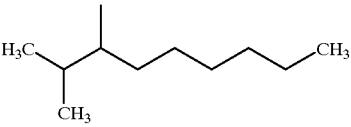 | H | 58 | 0.44 b) |
| 11 | 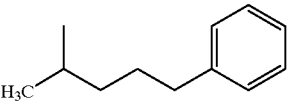 | H | 95 | 0.54 a) |
| 12 | 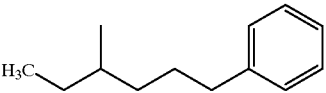 | H | 71 | 0.58 a) |
| 13 | 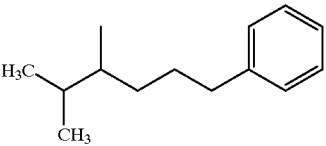 | H | 63 | 0.59 a) |
| 14 | 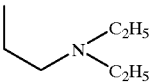 | H | 50 | 143 |
| 15 | 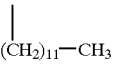 | H | 42 | 80 |
| 16 | 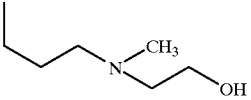 | H | 56 | 188 |
| 17 | 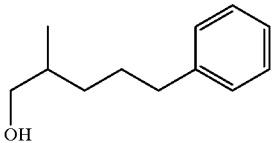 | H | 23 | 0.33 a) |
| 18 | 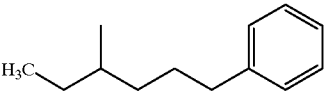 | 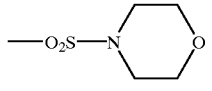 | 80 | 165 |

TABLE II-continued

|  | | | | |
|---|---|---|---|---|
| 1) Example No. | A. | D | 2) Yield (%) | 3) M.p.(° C.)/R$_f$ |
| 19 | H$_3$C—CH(CH$_3$)—CH(CH$_3$)—CH$_2$—CH$_2$—C$_6$H$_5$ | —O$_2$S—N(morpholine) | 33 | 0.44 b) |
| 20 | H$_3$C—CH(OH)—CH(CH$_3$)—CH$_2$—CH$_2$—C$_6$H$_5$ | —O$_2$S—N(morpholine) | 25 | 172 |
| 21 | H$_3$C—CH(CH$_3$)—CH$_2$—CH$_2$—CH$_2$—C$_6$H$_5$ | —O$_2$S—N(morpholine) | 57 | 170 | a) Mobile phase: CH$_2$Cl$_2$/MeOH 10:1
b) Mobile phase: Toluene/acetone 1:1

EXAMPLE 22

9-(2-Methanesulfonyloxy-3-Nonyl)-2-(2-n-Propoxyphenyl)Purin-6-One

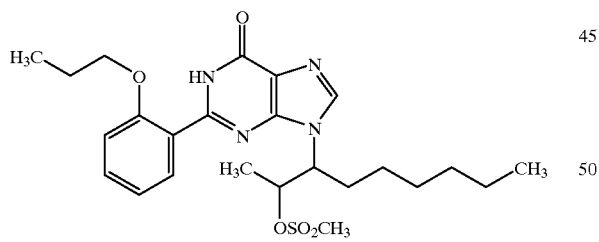

412 mg (1 mmole) of 9-(2-hydroxy-3-nonyl)-2-(2-n-propoxyphenyl)purin-6-one (Example 3) is cooled to 0° C. in 10 ml of CH$_2$Cl$_2$. After adding 0.5 ml of triethylamine, 138 mg (1.2 mmoles) of methanesulfonyl chloride in 2 ml of CH$_2$Cl$_2$ is added dropwise and stirring is continued for 30 minutes longer. The mixture is poured into 20 ml of ice water, the organic phase is separated, and the aqueous phase is extracted once more with 20 ml of CH$_2$Cl$_2$. The combined CH$_2$Cl$_2$ phases are dried over Na$_2$SO$_4$, evaporated under vacuum, and the oily residue is crystallized by trituration in ether.

M.p.: 158° C.

EXAMPLE 23

9-(2-Methanesulfonyloxy-5-Phenyl-3-Pentyl)-2-(2-N-Propoxyphenyl)Purin-6-One

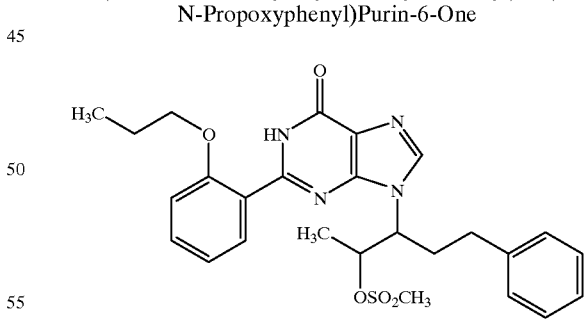

The title compound is prepared analogously to the method of Example 22, starting with 9-(2-hydroxy-5-phenyl-3-methyl)-2-(2-n-propoxyphenyl)purin-6-one [sic] (Example 4).

R$_f$=0.52 (CH$_2$Cl$_2$/CH$_3$OH 10:1)

EXAMPLE 24

9-(2-Methanesulfonyloxy-6-Phenyl-3-Hexyl)-2-(2-N-Propoxyphenyl)Purin-6-One

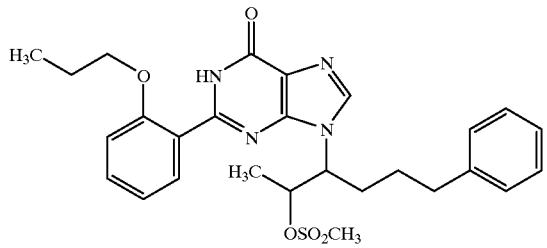

The title compound is prepared analogously to the method of Example 22, starting with 9-(2-hydroxy-6-phenyl-3-hexyl)-2-(2-n-propoxyphenyl)purin-6-one (Example 5).

$R_f$=0.52 (CH$_2$Cl$_2$/CH$_3$OH 10:1)

EXAMPLE 25

9-(2-Methanesulfonyloxy-7-Phenyl-3-Heptyl)-2-(2-N-Propoxyphenyl)Purin-6-One

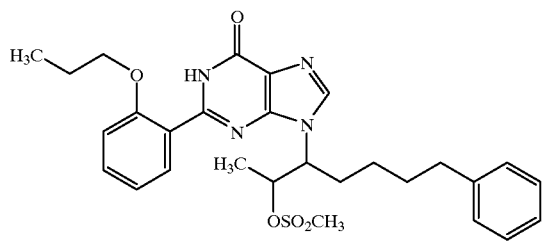

The title compound is prepared analogously to the method of Example 22, starting with 9-(2-hydroxy-7-phenyl-3-heptyl)-2-(2-n-propoxyphenyl)purin-6-one (Example 6).

$R_f$=0.55 (CH$_2$Cl$_2$/CH$_3$OH 10:1)

EXAMPLE 26

9-(2-Methanesulfonyloxy-8-Phenyl-3-Octyl)-2-(2-N-Propoxyphenyl)Purin-6-One

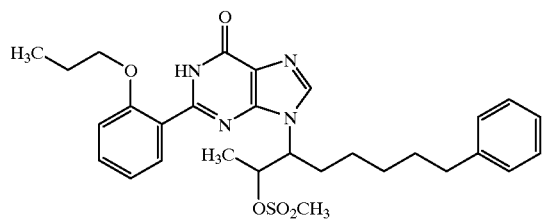

The title compound is prepared analogously to the method of Example 22, starting with 9-(2-hydroxy-8-phenyl-3-octyl)-2-(2-n-propoxyphenyl)purin-6-one (Example 7).

$R_f$=0.58 (CH$_2$Cl$_2$/CH$_3$OH 10:1)

EXAMPLE 27

9-(1-Methanesulfonyloxy-5-Phenyl-2-Pentyl)-2-(2-N-Propoxyphenyl)Purin-6-One

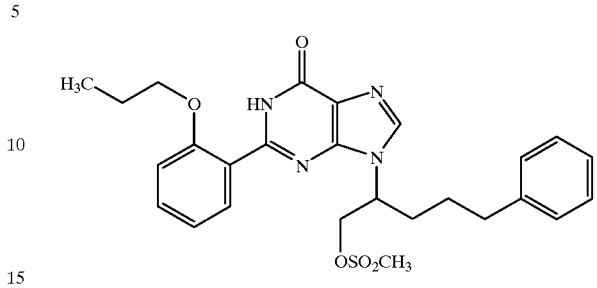

The title compound is prepared analogously to the method of Example 22, starting with 9-(1-hydroxy-5-phenyl-3-pentyl)-2-(2-n-propoxyphenyl)purin-6-one (Example 17).

$R_f$=0.49 (CH$_2$Cl$_2$/CH$_3$OH 10:1)

EXAMPLE 28

9-(2-Methanesulfonyloxy-3-Nonyl)-2-(2-N-Propoxy-5-Morpholinosulfonylphenyl)Purin-6-One

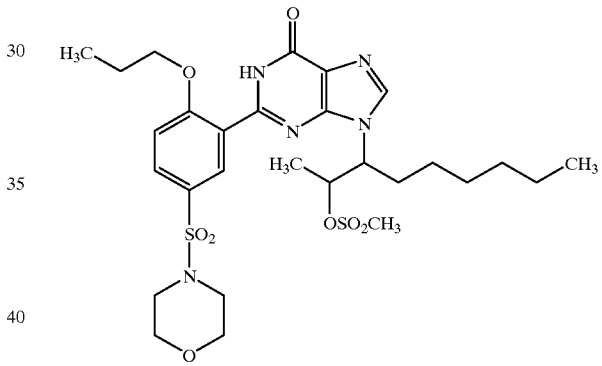

The title compound is prepared analogously to the method of Example 22, starting with 9-(2-hydroxy-3-nonyl)-2-(2-n-propoxy-5-morpholinosulfonylphenyl)purin-6-one (Example 20).

$R_f$=0.48 (CH$_2$Cl$_2$/CH$_3$OH 10:1)

EXAMPLE 29

9-(2-Azido-3-Nonyl)-2-(2-N-Propoxyphenyl)Purin-6-One

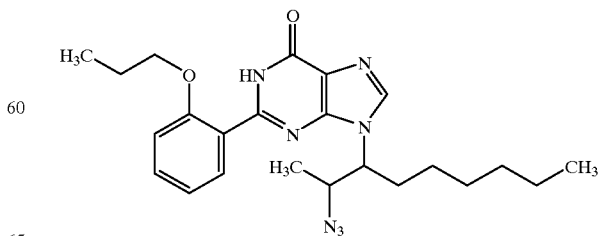

474 mg (1 mmole) of 9-(2-methanesulfonyloxy-3-nonyl)-2-(2-n-propoxyphenyl)purin-6-one (Example 22) and 78 mg (1.2 mmoles) of sodium azide are stirred in 5 ml of DMF for 6 h (TLC control) at 100° C. After cooling, 20 ml of ethyl acetate is added, and the mixture is extracted 3 times with 50-ml portions of water and once with 50 ml of saturated NaCl solution. After drying over $Na_2SO_4$, the organic phase is evaporated under vacuum, and the residue is purified by flash chromatography (eluant: toluene/acetone 4:1).

$R_f$=0.64 ($CH_2Cl_2/CH_3OH$ 10:1)

EXAMPLE 30

9-(2-Azido-5-Phenyl-3-Pentyl)-2-(2-N-Propoxyphenyl)Purin-6-One

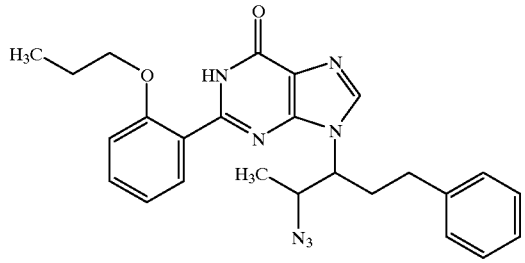

The title compound is prepared analogously to the method of Example 29, starting with 9-(2-methanesulfonyloxy-5-phenyl-3-pentyl)-2-(2-n-propoxyphenyl)purin-6-one (Example 23).

$R_f$=0.54 ($CH_2Cl_2/CH_3OH$ 10:1)

EXAMPLE 31

9-(2-Azido-6-Phenyl-3-Hexyl)-2-(2-N-Propoxyphenyl)Purin-6-One

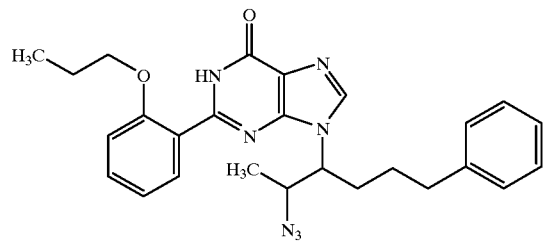

The title compound is prepared analogously to the method of Example 29, starting with 9-(2-methanesulfonyloxy-6-phenyl-3-hexyl)-2-(2-n-propoxyphenyl)purin-6-one (Example 24).

$R_f$=0.55 ($CH_2Cl_2/CH_3OH$ 10:1)

EXAMPLE 32

9-(2-Azido-7-Phenyl-3-Heptyl)-2-(2-N-Propoxyphenyl)Purin-6-One

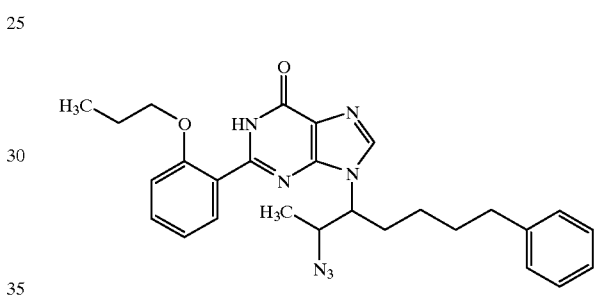

The title compound is prepared analogously to the method of Example 29, starting with 9-(2-methanesulfonyloxy-7-phenyl-3-heptyl)-2-(2-n-propoxyphenyl)purin-6-one (Example 25).

$R_f$=0.6 ($CH_2Cl_2/CH_3OH$ 10:1)

EXAMPLE 33

9-(2-Azido-8-Phenyl-3-Octyl)-2-(2-N-Propoxyphenyl)Purin-6-One

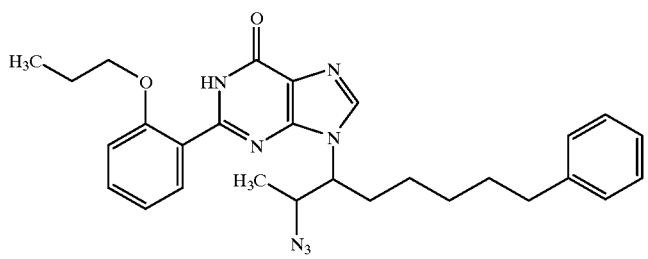

The title compound is prepared analogously to the method of Example 29, starting with 9-(2-methanesulfonyloxy-8-phenyl-3-octyl)-2-(2-n-propoxyphenyl)purin-6-one (Example 26).

$R_f$=0.61 (CH$_2$Cl$_2$/CH$_3$OH 10:1)

EXAMPLE 34

9-(1-Azido-5-Phenyl-2-Pentyl)-2-(2-N-Propoxyphenyl)Purin-6-One

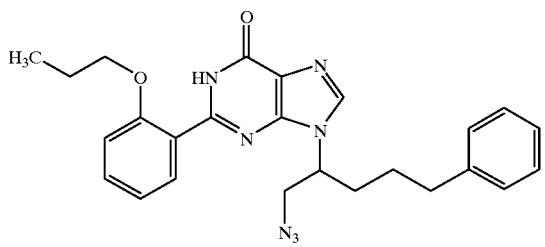

The title compound is prepared analogously to the method of Example 29, starting with 9-(1-methanesulfonyloxy-5-phenyl-2-pentyl)-2-(2-n-propoxyphenyl)purin-6-one (Example 27).

$R_f$=0.56 (CH$_2$Cl$_2$/Me$_3$OH 10:1)

EXAMPLE 35

9-(2-Azido-3-Nonyl)-2-(2-N-Propoxyphenyl-5-Morpholinosulfonylphenyl)Purin-6-One

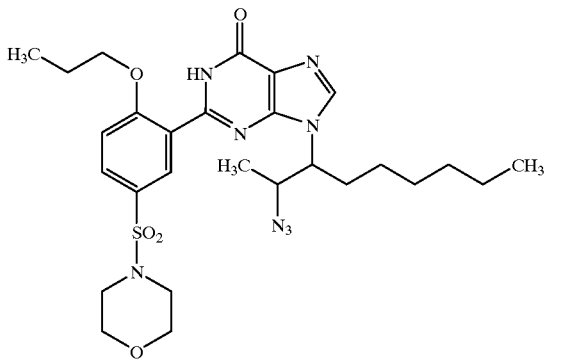

The title compound is prepared analogously to the method of Example 29, starting with 9-(2-methanesulfonyloxy-3-nonyl)-2-(2-n-propoxyphenyl-5-morpholinosulfonylphenyl)purin-6-one (Example 28).

$R_f$=0.55 (CH$_2$Cl$_2$/CH$_3$OH 10:1)

EXAMPLE 36

9-(2-Amino-3-Nonyl)-2-(2-N-Propoxyphenyl)Purin-6-One

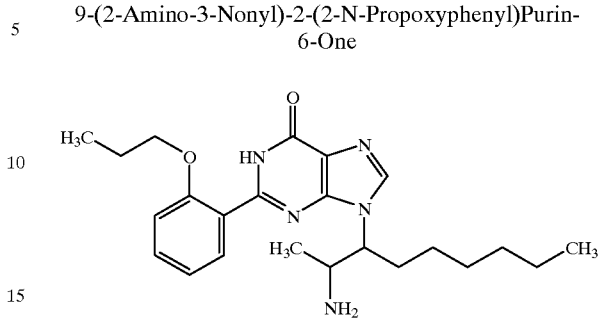

5.3 g (12.13 mmoles) of 9-(2-azido-3-nonyl-2-(2-n-propoxyphenyl)purin-6-one (Example 29) is hydrogenated in 70 ml of absolute methanol in the presence of 0.1 g of Pd/C (10%), with hydrogen at atmospheric pressure and room temperature. After 4 hours, the catalyst is filtered off, the solvent is distilled off, and the residue is purified on silica gel by flash chromatography (eluant: CH$_2$CH$_2$/CH$_3$OH 20:1).

$R_f$=0.28 (CH$_2$Cl$_2$/CH$_3$OH 10:1)

EXAMPLE 37

9-(2-Acetylamino-3-Nonyl)-2-(2-N-Propoxyphenyl)Purin-6-One

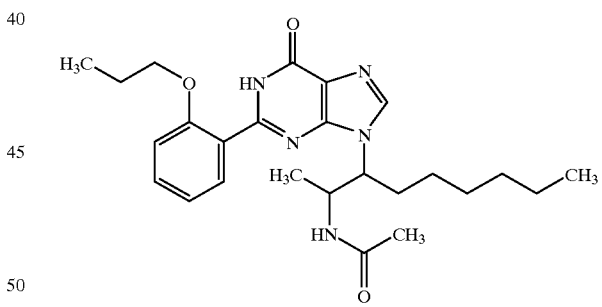

210 mg (0.5 mmole) of 9-(2-amino-3-nonyl)-2-(2-n-propoxyphenyl)purin-6-one (Example 36) is dissolved in 20 ml of absolute CH$_2$Cl$_2$. 101 mg (1 mmole) of triethylamine is added; 78 mg (1 mmole) of acetyl chloride in 2 ml of absolute CH$_2$Cl$_2$ is then added dropwise. After 1 hour at room temperature, the organic phase is extracted with 10 ml of 2 N HCl and with 10 ml of saturated NaHCO$_3$ solution. After drying the organic phase over Na$_2$SO$_4$, the solvent is evaporated under vacuum, and the residue is purified by flash chromatography (eluant: CH$_2$Cl$_2$/CH$_3$OH 40:1).

$R_f$=0.37 (CH$_2$Cl$_2$/CH$_3$OH 10:1)

EXAMPLE 38

9-(2-Benzoylamino-3-Nonyl)-2-(2-N-Propoxyphenyl)Purin-6-One

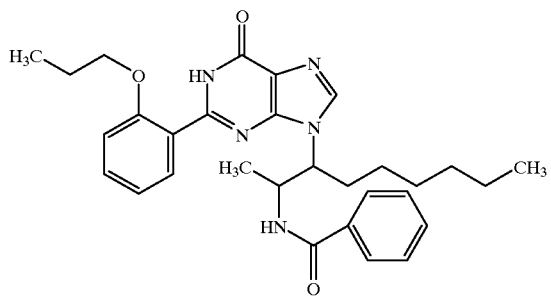

The title compound is prepared analogously to the method of Example 37, starting with 9-(2-amino-3-nonyl)-2-(2-n-propoxyphenyl)purin-6-one (Example 36) and benzoyl chloride.

M.p.: 184° C. (toluene)

EXAMPLE 39

9-(2-Methanesulfonylamino-3-Nonyl)-2-(2-N-Propoxyphenyl)Purin-6-One

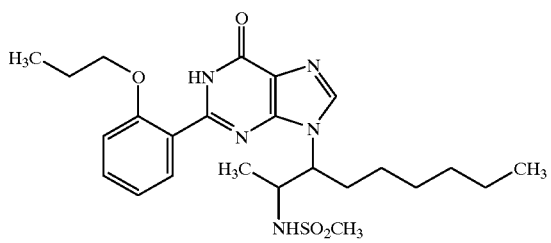

The title compound is prepared analogously to the method of Example 37, starting with 9-(2-amino-3-nonyl)-2-(2-n-propoxyphenyl)purin-6-one (Example 36) and methanesulfonyl chloride.

$R_f$=0.46 ($CH_2Cl_2/CH_3OH$ 10:1)

EXAMPLE 40

9-(2-Benzenesulfonylamino-3-Nonyl)-2-(2-N-Propoxyphenyl)Purin-6-One

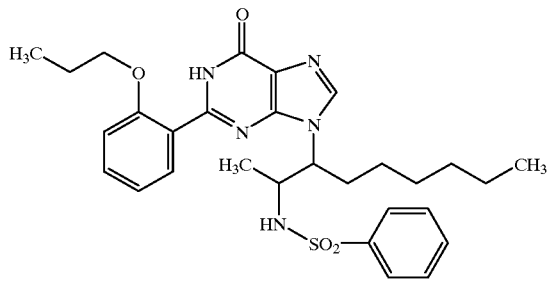

The title compound is prepared analogously to the method of Example 37, starting with 9-(2-amino-3-nonyl)-2-(2-n-propoxyphenyl)purin-6-one (Example 36) and benzenesulfonyl chloride.

M.p.: 112° C. (toluene/ether)

EXAMPLE 41

9-(2-Acetoxy-3-Nonyl)-2-(2-N-Propoxyphenyl)Purin-6-One

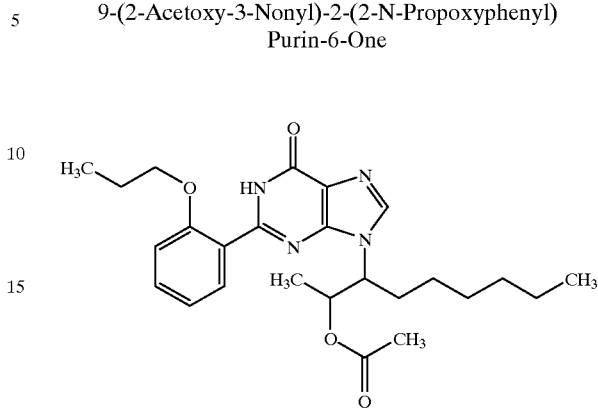

206 mg (0.5 mmole) of 9-(2-hydroxy-3-nonyl)-2-(2-n-propoxyphenyl)purin-6-one (Example 3), 47 mg (0.6 mmole) of acetyl chloride, 47 mg (0.6 mmole) of pyridine, and 5 mg of DMAP are stirred for 1 hour at 25° C. in 10 ml of absolute $CH_2Cl_2$ and then for 1 hour at 40° C. The mixture is extracted twice with 10-ml portions of 2 N HCl and twice with 10-ml portions of saturated $NaHCO_3$ solution and washed once with saturated NaCl solution. After drying the organic phase over $Na_2SO_4$, the solvent is evaporated under vacuum, and the residue is dried under high vacuum.

$R_f$=0.53 ($CH_2Cl_2/CH_3OH$ 100:1)

EXAMPLE 42

9-(1-Acetoxy-2-Octyl)-2-(2-N-Propoxyphenyl)Purin-6-One

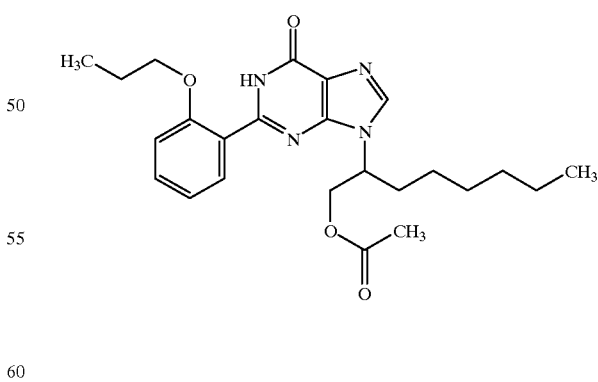

The title compound is prepared analogously to the method of Example 41, starting with 9-(1-hydroxy-2-octyl)-2-(2-n-propoxyphenyl)purin-6-one (Example 2).

$R_f$=0.52 ($CH_2Cl_2/CH_3OH$ 100:1)

EXAMPLE 43

9-(2-Benzoyloxy-3-Nonyl)-2-(2-N-Propoxyphenyl)Purin-6-One

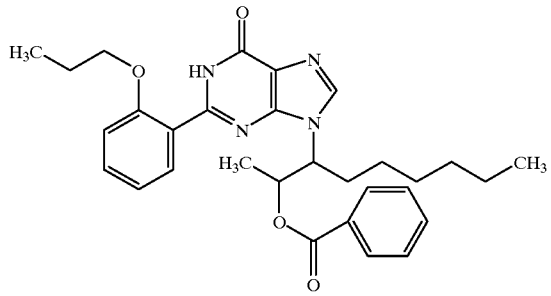

The title compound is prepared analogously to the method of Example 41, starting with 9-(2-hydroxy-3-nonyl)-2-(2-n-propoxyphenyl)purin-6-one (Example 3) and benzoyl chloride.

$R_f$=0.57 (CH$_2$Cl$_2$/CH$_3$OH 100:1)

EXAMPLE 44

9-(2-Methoxy-3-Nonyl)-2-(2-N-Propoxyphenyl)Purin-6-One

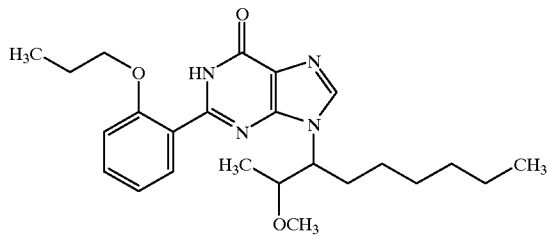

48 mg of 60% NaH (1.2 mmoles) is suspended at 20° C. in 2 ml of absolute THF. 206 mg (0.5 mmole) of 9-(2-hydroxy-3-nonyl)-2-(2-n-propoxyphenyl)purin-6-one (Example 3) in 3 ml of absolute THF is added dropwise. After 15 minutes at 20° C., 85 mg (0.6 mmole) of methyl iodide in 3 ml of absolute THF is added dropwise, and the mixture is stirred overnight at 20° C. The solvent is evaporated under vacuum in a rotary evaporator, and the residue is taken up in 10 ml of ethyl acetate and washed with 20 ml of water. After drying the organic phase over Na$_2$SO$_4$ it is evaporated in a rotary evaporator and the product is purified by column chromatography (eluant: toluene/acetone 5:1).

$R_f$=0.58 (CH$_2$Cl$_2$/CH$_3$OH 100:1)

EXAMPLE 45

9-(2-Ethoxycarbonylmethylenoxy-3-Nonyl)-2-(2-N-Propoxyphenyl)Purin-6-One

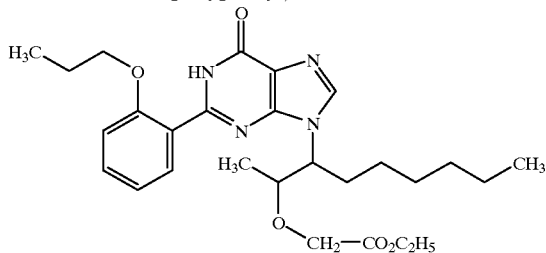

The title compound is prepared analogously to the method of Example 44, starting with 9-(2-hydroxy-3-nonyl)-2-(2-n-propoxyphenyl)purin-6-one (Example 3) and ethyl bromoacetate.

$R_f$=0.55 (CH$_2$Cl$_2$/CH$_3$OH 100:1)

EXAMPLE 46

9-(2-Carboxymethylenoxy-3-Nonyl)-2-(2-N-Propoxphenyl)Purin-6-One

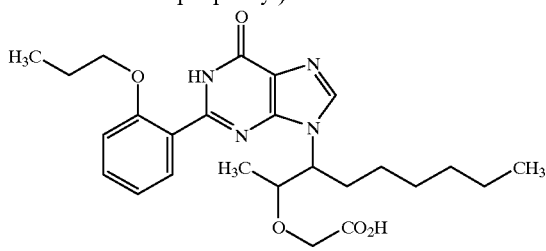

498 mg (1 mmole) of the ester from Example 45 is stirred for 1 hour at 20° C. in 4 ml of 1 N NaOH and 5 ml of MeOH. The methanol is distilled off under vacuum. After adding 5 ml of H$_2$O, the mixture is extracted with ethyl acetate. The aqueous phase is acidified with 4 ml of 2 N HCl and extracted twice with 10-ml portions of ethyl acetate. The combined ethyl acetate phases are dried over Na$_2$SO$_4$ and evaporated.

$R_f$=0.27 (CH$_2$Cl$_2$/CH$_3$OH 10:1)

EXAMPLE 47

9-(2-Aminocarbonylmethylenoxy-3-Nonyl)-2-(2-N-Propoxyphenyl)Purin-6-One

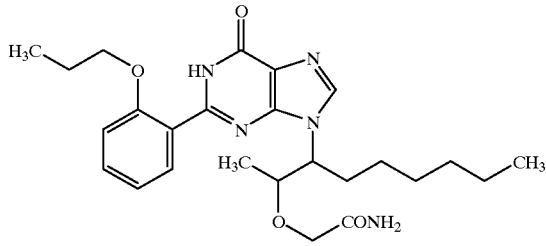

The title compound is prepared analogously to the method of Example 45, starting with 9-(2-hydroxy-3-nonyl)-2-(2-n-propoxyphenyl)purin-6-one (Example 3 ) and ethyl bromoacetamide.

$R_f$=0.26 (CH$_2$Cl$_2$/CH$_3$OH 10:1)

EXAMPLE 48

9-(2-Oxo-3-Nonyl)-2-(2-N-Propoxyphenyl)Purin-6-One

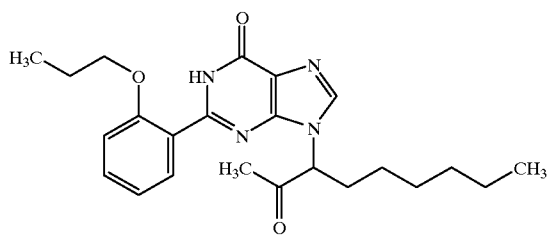

0.31 ml of absolute DMSO (4.4 mmoles) in 3 ml of absolute $CH_2Cl_2$ is added dropwise to 0.19 ml (2.2 mmoles) of oxalyl chloride in 5 ml of $CH_2Cl_2$ at $-60°$ C. over a period of 10 min, and stirring is continued for 20 min longer. 824 mg (2 mmoles) of 9-(2-hydroxy-3-methyl)-2-(2-n-propoxyphenyl)purin-6-one (Example 3) in 5 ml of absolute $CH_2Cl_2$ is then added dropwise over a period of 45 minutes, and stirring is continued for 1 hour longer at $-60°$ C. To this solution is added 1.39 ml (10 mmoles) of triethylamine in 5 ml of absolute $CH_2Cl_2$ over a period of 30 minutes, and stirring is continued for 15 minutes longer at $-60°$ C. The mixture is allowed to warm up to $20°$ C., 10 ml of $H_2O$ is added, the phases are separated, and the organic phase is washed with 20 ml of saturated NaCl solution. After drying over $Na_2SO_4$ the solvent is evaporated, and the residue is purified by flash chromatography (eluant: $CH_2Cl_2/CH_3OH$ 40:1).

M.p.: $83°$ C. (ether/cyclohexane)

EXAMPLE 49

9-(2-Ethoxyimino-3-Nonyl)-2-(2-N-Propoxyphenyl)Purin-6-One

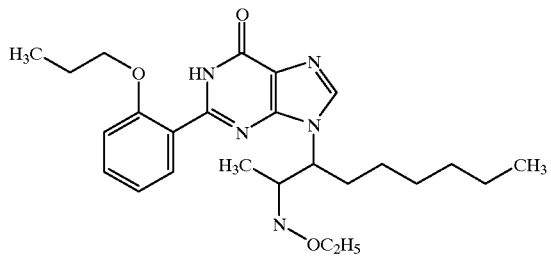

412 mg (1 mmole) of 9-(2-oxo-3-nonyl)-2-(2-n-propoxyphenyl)purin-6-one (Example 48) is dissolved in 10 ml of methanol, and 117 mg (1.2 mmoles) of ethoxylamine hydrochloride dissolved in 1.5 ml of water is added. The mixture is boiled under reflux for 2 hours, cooled, and evaporated under vacuum. The residue is taken up in 10 ml of ethyl acetate and washed with 10 ml of saturated $NaHCO_3$ solution. After drying the organic phase over $Na_2SO_4$, the solvent is distilled off under vacuum, and the residue is purified by flash chromatography (eluant: toluene/acetone 4:1).

$R_f = 0.53$ (toluene/acetone 1:1)

EXAMPLES 50, 51, 52 & 53

The oximes listed in Table III are prepared by this method using the appropriate hydroxylamine hydrochlorides (all oximes exist as cis/trans mixtures).

TABLE III

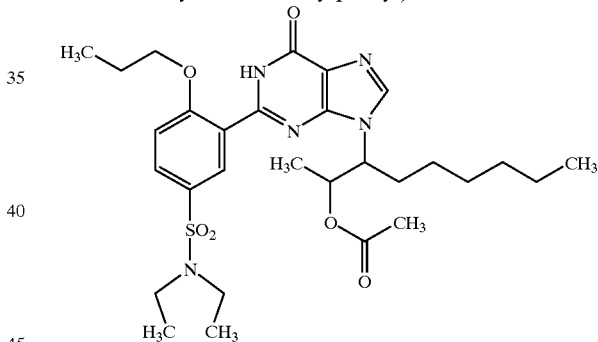

| 1) Example No. | 2) $R^{20}$ | 2) Yield (%) | 3) M.p.($°$ C.)/$R_f$ |
|---|---|---|---|
| 50 | H | 69.4 | 111 |
| 51 | $C(CH_3)_3$ | 79.4 | 0.56 a) |
| 52 | $-CH_2-C_6H_5$ | 98.4 | 0.55 a) |
| 53 | $-CH_2CH_2-N\begin{smallmatrix}C_2H_5\\C_2H_5\end{smallmatrix}$ | 70.2 | 0.29 b) |

1) Example No.
2) Yield (%)
3) M.p.($°$ C.)/$R_f$
a) Mobile phase: toluene/acetone 1:1
b) Mobile phase: $CH_2Cl_2$/MeOH 10:1

EXAMPLE 54

9-2-(2-Acetoxy-3-Nonyl)-2-(2-N-Propoxy-5-Diethylaminosulfonylphenyl)Purin-6-One 1.28 g (2.82 mmoles) of 9-(2-acetoxy-3-nonyl)-2-(2-n-propoxyphenyl)purin-6-one (Example 41) is added in portions at $0°$ C. to 4 ml of chlorosulfonic acid, and the mixture is stirred overnight at $20°$ C. The mixture is poured into 30 ml of ice water, and the aqueous phase is extracted twice with 20 ml portions of ethyl acetate. The combined organic phases are dried over $Na_2SO_4$, and the solvent is distilled off under vacuum.

Yield: 0.9 g (57.8%) $R_f$=0.52 ($CH_2Cl_2/CH_3OH$ 10:1)

The residue without further purification is taken up in 30 ml of absolute ethanol, 5.1 ml of diethylamine is added, and the mixture is stirred for 6 hours (TLC control) at $25°$ C. The ethanol is distilled off under vacuum, and the residue is taken up in 50 ml of ethyl acetate and washed twice with 50-ml portions of $H_2O$. After drying over $Na_2SO_4$, the organic phase is evaporated under vacuum, and the residue is purified by flash chromatography (eluant: toluene/acetone 3:1).

$R_f$=0.52 ($CH_2Cl_2/CH_3OH$ 10:1)

The compounds listed in Table IV are prepared analogously to the method of Example 54 from the appropriate purinone and the appropriate amine:

TABLE IV
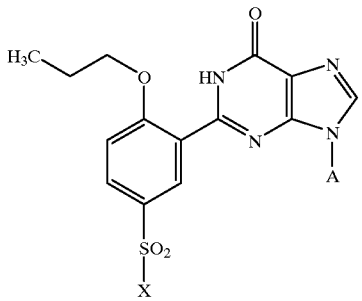
| 1) Example No. | X | A | 2) Yield (%) | 3) M.p.(° C.)/R$_f$ |
|---|---|---|---|---|
| 55 | 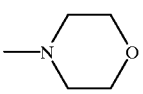 | 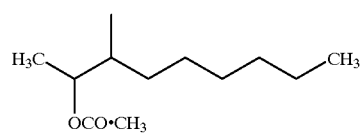 | 37.4 | 0.53 a) |
| 56 | 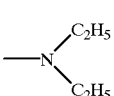 p | 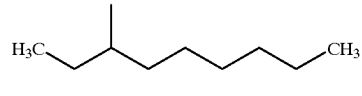 | 72.3 | 0.58 a) |
| 57 | 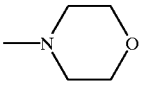 | 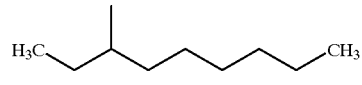 | 80.9 | 0.51 a) |
| 58 | 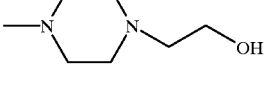 | 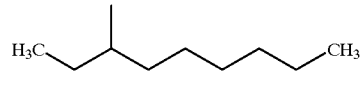 | 78.4 | 0.39 a) |
| 59 | 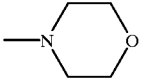 | 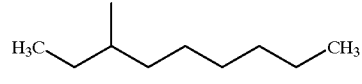 | 35.9 | 0.3 b) |
| 60 | 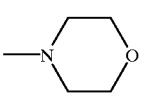 | 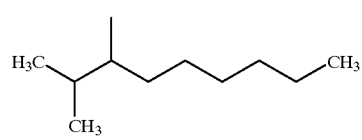 | 58 | 0.52 a) |
| 61 | 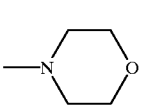 | 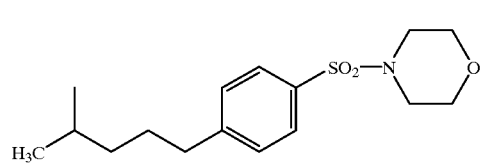 | 41 | 0.27 b) |

TABLE IV-continued
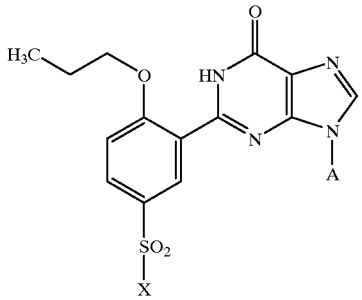
| 1) Example No. | X | A | 2) Yield (%) | 3) M.p.(° C.)/R$_f$ |
|---|---|---|---|---|
| 62 | 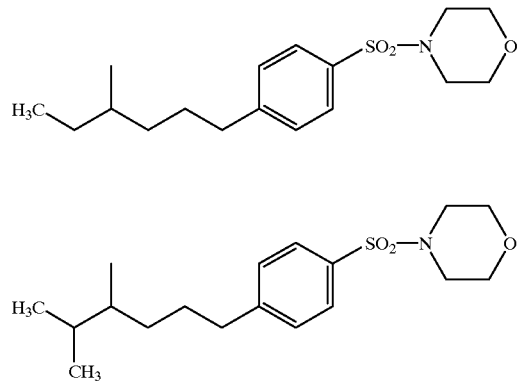 | 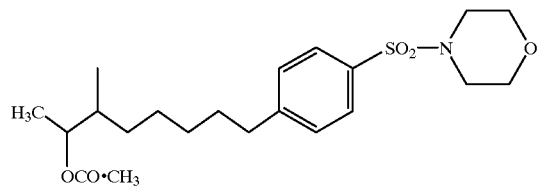 | 26.5 | 0.33 b) |
| 63 | (N-methylmorpholine) | (3-methyl branched chain) | 76.3 | 0.35 b) |
| 64 | (N-methylmorpholine) | (chain with OCO·CH$_3$) | 37 | 0.39 b) |
a) Mobile phase: CH$_2$Cl$_2$/CH$_3$OH 10:1
b) Mobile phase: toluene/acetone 1:1
1) Example No.
2) Yield (%)
3) M.p.(° C.)/R$_f$

EXAMPLE 65

9-(2-Hydroxy-3-Nonyl)-2-(2-N-Propoxy-5-Diethylaminosulfonylphenyl)Purin-6-One

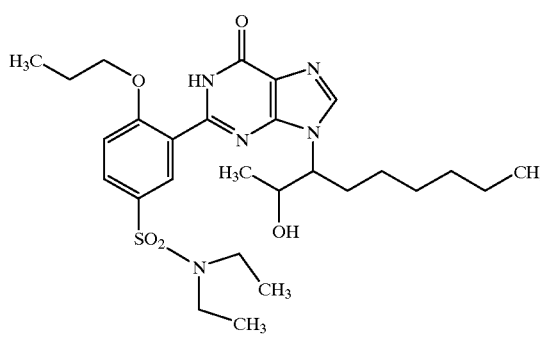

140 mg (0.24 mmole) of 5-(2-acetoxy-3-nonyl)-2-(2-n-propoxy-5-diethylaminosulfonylphenyl)purin-6-one (Example 54) is dissolved in 5 ml of methanol. After adding 0.5 ml of aqueous 1 N NaOH solution, the mixture is stirred for 2 hours at 25° C. 0.25 ml of aqueous 2 N HCl solution is added, the methanol is distilled off under vacuum, and 10 ml of ethyl acetate and 10 ml of water are added. The organic phase is separated, dried over $Na_2SO_4$, and evaporated. The residue is purified by flash chromatography (eluant: $CH_2Cl_2$/$CH_3OH$ 40:1).

$R_f$=0.47 ($CH_2Cl_2$/$CH_3OH$ 10:1)

EXAMPLE 66

9-(2-Hydroxy-3-Nonyl)-2-(2-N-Propoxy-5-Morpholinosulfonylphenyl)Purin-6-One

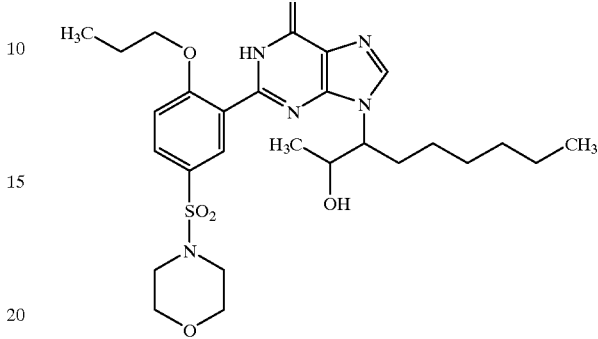

The title compound is prepared analogously to the method of Example 65 starting with 9-(2-acetoxy-3-nonyl)-2-(2-n-propoxy-5-morpholinosulfonylphenyl)purin-6-one (Example 55).

$R_f$=0.45 ($CH_2Cl_2$/$CH_3OH$ 10:1)

EXAMPLE 67

9-(2-Hydroxy-8-(4-Morpholinosulfonylphenyl)-3-Octyl)-2-(2-N-Propoxy-5-Morpholinosulfonylphenyl)Purin-6-One

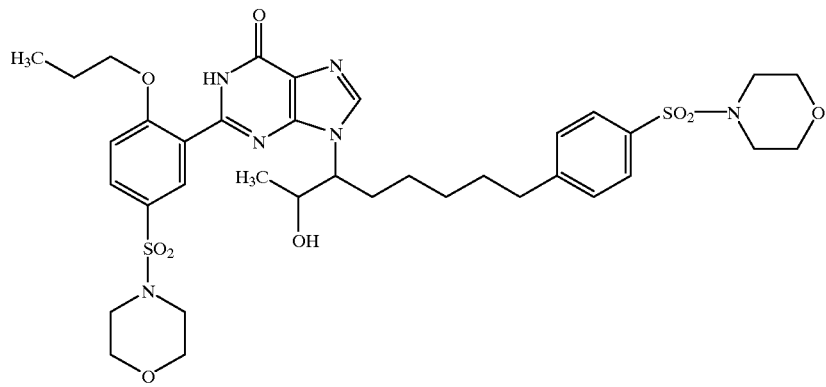

The title compound is prepared analogously to the method of Example 65 starting with 9-(2-acetoxy-8-(4-morpholinosulfonylphenyl)-3-octyl)-2-(2-n-propoxy-5-morpholinosulfonylphenyl)purin-6-one (Example 64).

$R_f$=0.35 (toluene/acetone 1:1)

EXAMPLE 68

9-(2-Oxo-3-Nonyl)-2-(2-N-Propoxy-5-Morpholinosulfonylphenyl)Purin-6-One

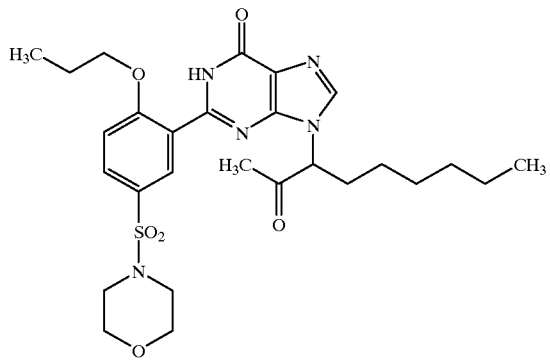

The title compound is prepared analogously to the method of Example 48 starting with 9-(2-hydroxy-3-nonyl)-2-(2-n-propoxy-5-morpholinosulfonylphenyl)purin-6-one (Example 66).

$R_f$=0.53 (CH$_2$Cl$_2$/CH$_3$OH 10:19)

EXAMPLE 69

9-(2-Oxo-8-(4-Morpholinosulfonylphenyl)-3-Octyl)-2-(2-N-Propoxy-5-Morpholinosulfonylphenyl)Purin-6-One

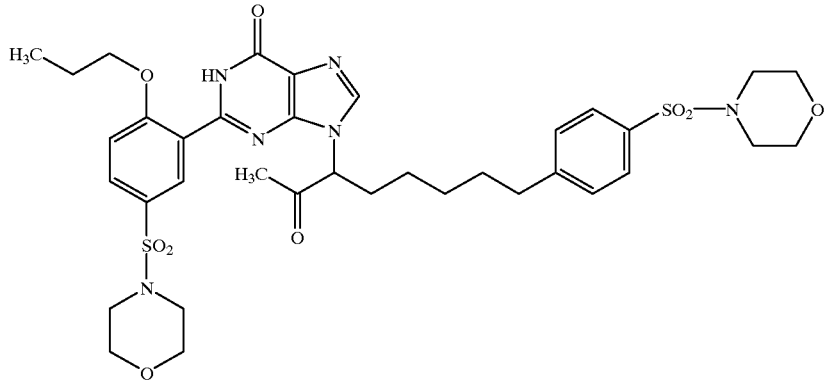

The title compound is prepared analogously to the method of Example 48 starting with 9-(2-hydroxy-8-(4-morpholinosulfonylphenyl)-3-octyl)-2-(2-n-propoxy-5-morpholinosulfonylphenyl)purin-6-one (Example 67).

$R_f$=0.41 (toluene/acetone 1:1)

EXAMPLE 70

9-(2-Oxo-6-Phenyl-3-Hexyl)-2-(2-N-Propoxy-5-Mopholinosulfonylphenyl)Purin-6-One

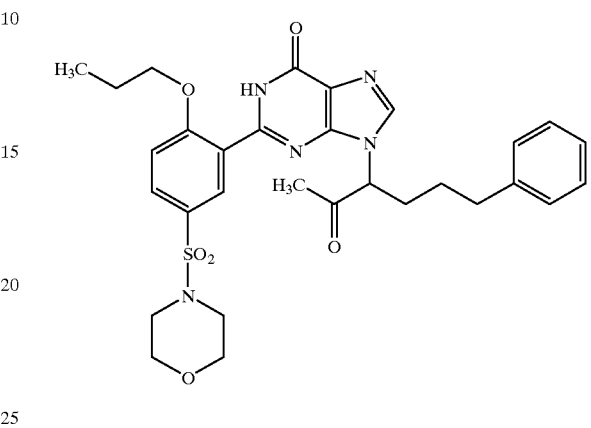

The title compound is prepared analogously to the method of Example 48 starting with 9-(2-hydroxy-6-phenyl-3-hexyl)-2-(2-n-propoxy-5-morpholinosulfonylphenyl)purin-6-one (from Example 20).

$R_f$=0.6 (CH$_2$Cl$_2$/CH$_3$OH 10:1)

It will be understood that various changes and modifications can be made in the details of procedure, formulation and use without departing from the spirit of the invention, especially as defined in the following claims.

We claim:

1. A method for inhibiting the growth of neoplastic cells comprising exposing the cells to an amount of a compound of Formula I effective to inhibit growth of said cells:

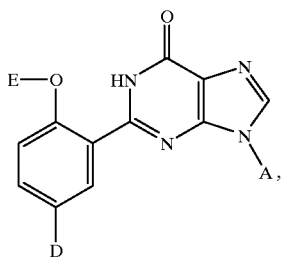

(I)

wherein A is selected from the group consisting of the formula

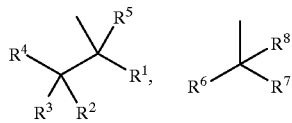

and $(CH_2)_a$—$CH_3$, and "a" is an integer from 9–15;

R$_1$ is selected from the group consisting of a straight-chain or branched alkyl group with 2 to 10 carbon atoms, which is optionally substituted by phenyl, which in turn may be substituted by halogen, nitro, cyano, straight-chain or branched alkyl with up to 6 carbon atoms, and by a group with the formula —$SO_2NR_9R_{10}$;

wherein $R_9$ and $R_{10}$ are the same or different, and are each selected from the group consisting of hydrogen, phenyl, and straight-chain or branched alkyl with up to 6 carbon atoms, which is optionally substituted by hydroxy, or together with the nitrogen atom $R_9$ and $R_{10}$ form a 5- to 6-membered saturated heterocyclic ring with up to 2 other hetero atoms from the group consisting of S, N, and/or O, which is also optionally substituted through a free N function by a straight-chain or branched alkyl with up to 6 carbon atoms, which in turn may be substituted by hydroxy, and/or is alkyl optionally substituted by a group with the formula —$NR_{11}R_{12}$;

wherein $R^2$ is selected from the group consisting of hydrogen, azido, straight-chain or branched alkyl with up to 6 carbon atoms and a group with the formula —$OR_{13}$, —$O$—$SO_2R_{14}$, and —$NR_{15}R_{16}$;

wherein $R_{13}$ is selected from the group consisting of hydrogen, a hydroxy-protecting group, straight-chain or branched alkyl with up to 6 carbon atoms, benzoyl and straight-chain or branched alkyl with up to 6 carbon atoms, which is optionally substituted by carboxy or straight-chain or branched alkoxycarbonyl with up to 6 carbon atoms, or by a group with the formula —$CO$—$NR_{17}R_{18}$;

wherein $R_{17}$ and $R_{18}$ are the same or different and are selected from the group consisting of hydrogen and straight-chain or branched alkyl with up to 4 carbon atoms, $R_{14}$ is selected from the group consisting of straight-chain or branched alkyl with up to 4 carbon atoms and phenyl;

$R_{15}$ and $R_{16}$ are the same or different and are selected from a group consisting of hydrogen, an amine-protecting group, straight-chain or branched alkyl or acyl, each with up to 6 carbon atoms, formyl, benzoyl, and a group with the formula —$SO_2R_{19}$, wherein $R_{19}$ has the meaning given above for $R_{14}$ and is the same as or different from it, $R_3$ is selected from a group consisting of hydrogen, or $R^2$ and $R^3$ together form a group of the formula =O or =N—$OR_{20}$;

wherein $R_{20}$ is selected from a group consisting of hydrogen and straight-chain or branched alkyl with up to 6 carbon atoms, which is optionally substituted by phenyl or by a group with the formula —$NR_{21}R_{22}$, wherein $R_{21}$ and $R_{22}$ are the same or different and are selected from a group consisting of hydrogen, phenyl, and straight-chain or branched alkyl with up to 6 carbon atoms, $R_4$ is selected from a group consisting of hydrogen and straight-chain or branched alkyl with up to 4 carbon atoms, $R_5$ and $R_8$ are the same or different and are selected from the group consisting of hydrogen and straight-chain or branched alkyl with up to 3 carbon atoms, $R_6$ is selected from a group consisting of hydrogen and straight-chain or branched alkyl with up to 5 carbon atoms, which is optionally substituted by hydroxy, $R_7$ is selected from the group consisting of straight-chain or branched alkyl with 2 to 8 carbon atoms, which is substituted by a group with the formula —$NR_{23}R_{24}$, wherein $R_{23}$ and $R_{24}$ are the same or different and are selected from the group consisting of hydrogen and straight-chain or branched alkyl with up to 5 carbon atoms, which is optionally substituted by hydroxy, or is optionally substituted by phenyl, which in turn is substituted by the group with the formula —$SO_2$—$NR_{25}R_{26}$;

wherein $R_{25}$ and $R_{26}$ have the meanings given above for $R_9$ and $R_{10}$;

D is selected from a group consisting of hydrogen and a group with the formula —$SO_2$—$NR_{27}R_{28}$;

wherein $R_{27}$ and $R_{28}$ are the same or different and have the meanings given above for $R_9$ and $R_{10}$, and are the same as them or different from them; and E is selected from a group consisting of straight-chain or branched alkyl with up to 8 carbon atoms, and their tautomers and salts.

2. The method of claim 1 wherein A is selected from a group consisting of the formula

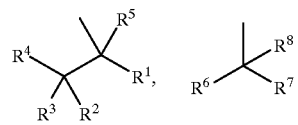

and $(CH_2)_a$—$CH_3$, wherein "a" is an integer from 9–13, $R_1$ is selected from a group consisting of straight-chain or branched alkyl group with 2 to 8 carbon atoms, which is optionally substituted by phenyl, which in turn may be substituted by fluorine, chlorine, bromine, nitro, cyano, straight-chain or branched alkyl with up to 4 carbon atoms, or by a group with the formula —$SO_2NR_{11}R_{12}$, wherein $R_9$ and $R_{10}$ are the same or different, and are selected from a group consisting of hydrogen, phenyl, and straight-chain or branched alkyl with up to 5 carbon atoms, which is optionally substituted by hydroxy, or together with the nitrogen atom they form a morpholinyl, pyrrolidinyl, piperidinyl, or piperazinyl ring, which is also optionally substituted through a free NH function by straight-chain or branched alkyl with up to 3 carbon atoms, which in turn may be substituted by hydroxy, and/or is alkyl optionally substituted by a group with the formula —$NR_{11}R_{12}$, wherein $R_{11}R_{12}$ have the meanings given above for $R_9$ and $R_{10}$ and are the same as them or different from them, $R_2$ is selected from a group consisting of hydrogen, azido, straight-chain or branched alkyl with up to 4 carbon atoms and a group with the formula —$OR_{13}$, —O—$SO_2R_{14}$, or —$NR_{15}R_{16}$, wherein $R_{13}$ is selected from a group consisting of hydrogen, benzyl, straight-chain or branched acyl with up to 4 carbon atoms, benzoyl and straight-chain or branched alkyl with up to 4 carbon atoms, which is optionally substituted by carboxy or straight-chain or branched alkoxycarbonyl with up to 4 carbon atoms, or by a group with the formula —CO—$NR_{17}R_{18}$, wherein $R_{17}R_{18}$ are the same or different and are selected from a group consisting of hydrogen and straight-chain or branched alkyl with up to 3 carbon atoms, $R_{14}$ is selected from a group consisting of straight-chain or branched alkyl with up to 3 carbon atoms and phenyl, $R_{15}$ and $R_{16}$ are the same or different and are selected from a group consisting of hydrogen, t-butoxycarbonyl, benzyloxycarbonyl, or straight-chain or branched alkyl and acyl, each with up to 4 carbon atoms, formyl, benzoyl, or a group with the formula —$SO_2R_{19}$, wherein $R_{19}$ has the meaning given above for $R_{14}$ and is the same as or different from it, $R_3$ is selected from a group consisting of hydrogen, or $R_2$ and $R_3$ together form a group of the formula =O or =N—$OR_{20}$, wherein $R_{20}$ is selected from a group consisting of hydrogen and straight-chain or branched alkyl with up to 4 carbon atoms, which is optionally substituted by phenyl or by a group with the formula —$NR_{21}R_{22}$, wherein $R_{21}$ and $R_{22}$ are the same or different and stand for hydrogen, phenyl, and straight-chain or branched alkyl with up to 4 carbon atoms, $R_4$ is selected from a group consisting of hydrogen and straight-chain or branched alkyl with up to 3 carbon atoms, $R_5$ and $R_8$ are the same or different and selected from the group consisting of hydrogen and methyl, $R_6$ is selected from the group consisting of hydrogen and straight-chain or branched alkyl with up to 3 carbon atoms, which is optionally substituted by hydroxy, $R_7$ is selected from the group consisting of straight-chain or branched alkyl with 2 to 6 carbon atoms, which is substituted by a group with the formula —$NR_{23}R_{24}$, wherein $R_{23}$ and $R_{24}$ are the same or different and are selected from the group consisting of hydrogen and straight-chain or branched alkyl with up to 4 carbon atoms, which is optionally substituted by hydroxy, or is optionally substituted by phenyl, which in turn is substituted by a group with the formula —$SO_2$—$NR^{25}R^{26}$, wherein $R_{25}$ and $R_{26}$ are the same or different and have the meanings given above for $R_9$ and $R_{10}$;

D is selected from a group consisting of hydrogen and from a group with the formula —$SO_2$—$NR^{27}R^{28}$;

wherein $R_{27}$ and $R_{28}$ are the same or different and have the meanings given above for $R_9$ and $R_{10}$, and are the same as them or different from them, E is selected from a group consisting of straight-chain or branched alkyl with up to 6 carbon atoms, and their tautomers and salts.

3. The method of claim 2 wherein:

A is selected from a group with the formula

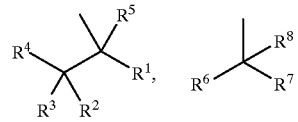

and $(CH_2)_a$—$CH_3$, wherein "a" is selected from a group consisting of a number 9, 10, 11, or 12, $R_1$ is selected from a group consisting of a straight-chain or branched alkyl group with 2 to 7 carbon atoms, which is optionally substituted by phenyl, which in turn may be substituted by fluorine, chlorine, bromine, nitro, cyano, straight-chain or branched alkyl with up to 3 carbon atoms, or by a group with the formula —$SO_2NR_9R_{10}$;

wherein $R_9$ and $R_{10}$ are the same or different, and are selected from a group consisting of hydrogen, phenyl, and straight-chain or branched alkyl with up to 4 carbon atoms, which is optionally substituted by hydroxy, or together with the nitrogen atom they form a morpholinyl, pyrrolidinyl, piperidinyl, or piperazinyl ring, which is also optionally substituted through a free NH function by straight-chain or branched alkyl with up to 3 carbon atoms, which in turn may be substituted by hydroxy, and/or is alkyl optionally substituted by a group with the formula —$NR_{11}R_{12}$ wherein $R_{11}$ and $R_{12}$ have the meanings given above for $R^9$ and $R_{10}$ and are the same as them or different from them, $R_2$ is selected from a group consisting of hydrogen, azido, straight-chain or branched alkyl with up to 3 carbon atoms and a group with the formula —$OR_{13}$, —O—$SO_2R_{14}$, or —$NR_{15}R_{16}$, wherein $R_{13}$ is selected from a group consisting of hydrogen, straight-chain or branched acyl with up to 3 carbon atoms, benzoyl and straight-chain or branched alkyl with up to 3 carbon atoms, which is optionally substituted by carboxy or straight-chain or branched alkoxycarbonyl with up to 3 carbon atoms, or by a group with the formula —CO—$NR_{17}R_{18}$, wherein $R_{17}$ and $R_{18}$ are the same or different and are selected from the group consisting of hydrogen and lower alkyl;

$R_{14}$ is selected from a group consisting of straight-chain or branched alkyl with up to 3 carbon atoms and phenyl, $R_{15}$ and $R_{16}$ are the same or different and are selected from a group consisting of hydrogen, t-butoxycarbonyl, straight-chain or branched alkyl or acyl, each with up to 3 carbon atoms, formyl, benzoyl, and a group with the formula —$SO2R_{19}$, wherein $R_{19}$ has the meaning given above for $R_{14}$ and is the same as or different from it, $R_3$ is selected from a group consisting of hydrogen, or $R_2$ and $R_3$ together form a group with the formula =O or =N—$OR_{20}$, wherein $R_{20}$ is selected from a group consisting of hydrogen and straight-chain or branched alkyl with up to 4 carbon atoms, which is optionally substituted by phenyl or by a group with the formula —$NR_{21}R_{22}$, wherein $R_{21}$ and $R_{22}$ are the same or different and are selected from a group consisting of hydrogen, phenyl, and straight-chain or branched alkyl with up to 3 carbon atoms, $R_4$ is selected from a group consisting of hydrogen and straight-chain or branched alkyl with up to 3 carbon atoms, $R_5$ and $R_8$ are the same or different and are selected from a group consisting of hydrogen and methyl, $R_6$ is selected from a group consisting of hydrogen and straight-chain or branched alkyl with up to 3 carbon atoms, which is optionally substituted by hydroxy, $R_7$ is selected from a group consisting of straight-chain or branched alkyl with 2 to 6 carbon atoms, which is substituted by a group with the formula —$NR_{23}R_{24}$, wherein $R_{23}$ and $R_{24}$ are the same or different and are selected from the groups consisting of hydrogen and a straight-chain or branched alkyl with up to 3 carbon atoms, which is optionally substituted by hydroxy, or is optionally substituted by phenyl, which in turn is substituted by the group with the formula —$SO_2$—$NR_{25}R_{26}$, wherein $R_{25}$ and $R_{26}$ have the meanings given above for $R_9$ and $R_{10}$, D is selected from a group consisting of hydrogen and from a group with the formula —$SO_2$—$NR_{27}R_{28}$, wherein $R_{27}$ and $R_{28}$ are the same or different and have the meanings given above for $R_9$ and $R_{10}$, and are the same as them or different from them, E is selected from a group consisting of straight-chain or branched alkyl with up to 5 carbon atoms, and their tautomers and salts.

4. A method of treating precancerous lesions in a mammal comprising administering to said mammal a pharmacologically effective amount of a compound of Formula I:

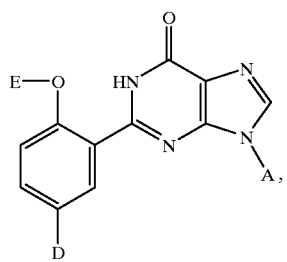

(I)

wherein A is selected from the group consisting of the formula

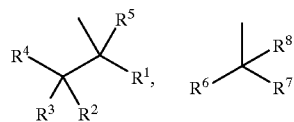

and $(CH_2)_a$–$CH_3$, and "a" is an integer from 9–15;

$R_1$ is selected from the group consisting of a straight-chain or branched alkyl group with 2 to 10 carbon atoms, which is optionally substituted by phenyl, which in turn may be substituted by halogen, nitro, cyano, straight-chain or branched alkyl with up to 6 carbon atoms, and by a group with the formula —$SO_2NR_9R_{10}$;

wherein $R_9$ and $R_{10}$ are the same or different, and are each selected from the group consisting of hydrogen, phenyl, and straight-chain or branched alkyl with up to 6 carbon atoms, which is optionally substituted by hydroxy, or together with the nitrogen atom $R_9$ and $R_{10}$ form a 5- to 6-membered saturated heterocyclic ring with up to 2 other hetero atoms from the group consisting of S, N, and/or O, which is also optionally substituted through a free N function by a straight-chain or branched alkyl with up to 6 carbon atoms, which in turn may be substituted by hydroxy, and/or is alkyl optionally substituted by a group with the formula —$NR_{11}R_{12}$;

wherein $R^2$ is selected from the group consisting of hydrogen, azido, straight-chain or branched alkyl with up to 6 carbon atoms and a group with the formula —$OR_{13}$, —$O$—$SO_2R_{14}$, and —$NR_{15}R_{16}$;

wherein $R_{13}$ is selected from the group consisting of hydrogen, a hydroxy-protecting group, straight-chain or branched alkyl with up to 6 carbon atoms, benzoyl and straight-chain or branched alkyl with up to 6 carbon atoms, which is optionally substituted by carboxy or straight-chain or branched alkoxycarbonyl with up to 6 carbon atoms, or by a group with the formula —$CO$—$NR_{17}R_{18}$;

wherein $R_{17}$ and $R_{18}$ are the same or different and are selected from the group consisting of hydrogen and straight-chain or branched alkyl with up to 4 carbon atoms, $R_{14}$ is selected from the group consisting of straight-chain or branched alkyl with up to 4 carbon atoms and phenyl;

$R_{15}$ and $R_{16}$ are the same or different and are selected from a group consisting of hydrogen, an amine-protecting group, straight-chain or branched alkyl or acyl, each with up to 6 carbon atoms, formyl, benzoyl, and a group with the formula —$SO_2R_{19}$, wherein $R_{19}$ has the meaning given above for $R_{14}$ and is the same as or different from it, $R_3$ is selected from a group consisting of hydrogen, or $R^2$ and $R^3$ together form a group of the formula =O or =N—$OR_{20}$;

wherein $R_{20}$ is selected from a group consisting of hydrogen and straight-chain or branched alkyl with up to 6 carbon atoms, which is optionally substituted by phenyl or by a group with the formula —$NR_{21}R_{22}$, wherein $R_{21}$ and $R_{22}$ are the same or different and are selected from a group consisting of hydrogen, phenyl, and straight-chain or branched alkyl with up to 6 carbon atoms, $R_4$ is selected from a group consisting of hydrogen and straight-chain or branched alkyl with up to 4 carbon atoms, $R_5$ and $R_8$ are the same or different and are selected from the group consisting of hydrogen and straight-chain or branched alkyl with up to 3 carbon atoms, $R_6$ is selected from a group consisting of hydrogen and straight-chain or branched alkyl with up to 5 carbon atoms, which is optionally substituted by hydroxy, $R_7$ is selected from the group consisting of straight-chain or branched alkyl with 2 to 8 carbon atoms, which is substituted by a group with the formula —$NR_{23}R_{24}$, wherein $R_{23}$ and $R_{24}$ are the same or different and are selected from the group consisting of hydrogen and straight-chain or branched alkyl with up to 5 carbon atoms, which is optionally substituted by hydroxy, or is optionally substituted by phenyl, which in turn is substituted by the group with the formula —SO$_2$—NR$_{25}$R$_{26}$;

wherein R$_{25}$ and R$_{26}$ have the meanings given above for R$_9$ and R$_{10}$;

D is selected from a group consisting of hydrogen and a group with the formula —SO$_2$—NR$_{27}$R$_{28}$;

wherein R$_{27}$ and R$_{28}$ are the same or different and have the meanings given above for R$_9$ and R$_{10}$, and are the same as them or different from them; and E is selected from a group consisting of straight-chain or branched alkyl with up to 8 carbon atoms, and their tautomers and salts.

5. The method of claim 4 wherein A is selected from a group consisting of the formula

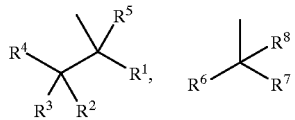

and (CH$_2$)$_a$—CH$_3$, wherein "a" is an integer from 9–13,

R$_1$ is selected from a group consisting of straight-chain or branched alkyl group with 2 to 8 carbon atoms, which is optionally substituted by phenyl, which in turn may be substituted by fluorine, chlorine, bromine, nitro, cyano, straight-chain or branched alkyl with up to 4 carbon atoms, or by a group with the formula —SO$_2$NR$_{11}$R$_{12}$, wherein R$_9$ and R$_{10}$ are the same or different, and are selected from a group consisting of hydrogen, phenyl, and straight-chain or branched alkyl with up to 5 carbon atoms, which is optionally substituted by hydroxy, or together with the nitrogen atom they form a morpholinyl, pyrrolidinyl, piperidinyl, or piperazinyl ring, which is also optionally substituted through a free NH function by straight-chain or branched alkyl with up to 3 carbon atoms, which in turn may be substituted by hydroxy, and/or is alkyl optionally substituted by a group with the formula —NR$_{11}$R$_{12}$, wherein R$_{11}$R$_{12}$ have the meanings given above for R$_9$ and R$_{10}$ and are the same as them or different from them, R$_2$ is selected from a group consisting of hydrogen, azido, straight-chain or branched alkyl with up to 4 carbon atoms and a group with the formula —OR$_{13}$, —O—SO$_2$R$_{14}$, or —NR$_{15}$R$_{16}$, wherein R$_{13}$ is selected from a group consisting of hydrogen, benzyl, straight-chain or branched acyl with up to 4 carbon atoms, benzoyl and straight-chain or branched alkyl with up to 4 carbon atoms, which is optionally substituted by carboxy or straight-chain or branched alkoxycarbonyl with up to 4 carbon atoms, or by a group with the formula —CO—NR$_{17}$R$_{18}$, wherein R$_{17}$R$_{18}$ are the same or different and are selected from a group consisting of hydrogen and straight-chain or branched alkyl with up to 3 carbon atoms, R$_{14}$ is selected from a group consisting of straight-chain or branched alkyl with up to 3 carbon atoms and phenyl, R$_{15}$ and R$_{16}$ are the same or different and are selected from a group consisting of hydrogen, t-butoxycarbonyl, benzyloxycarbonyl, or straight-chain or branched alkyl and acyl, each with up to 4 carbon atoms, formyl, benzoyl, or a group with the formula —SO$_2$R$_{19}$, wherein R$_{19}$ has the meaning given above for R$_{14}$ and is the same as or different from it, R$_3$ is selected from a group consisting of hydrogen, or R$_2$ and R$_3$ together form a group of the formula =O or =N—OR$_{20}$, wherein R$_{20}$ is selected from a group consisting of hydrogen and straight-chain or branched alkyl with up to 4 carbon atoms, which is optionally substituted by phenyl or by a group with the formula —NR$_{21}$R$_{22}$, wherein R$_{21}$ and R$_{22}$ are the same or different and stand for hydrogen, phenyl, and straight-chain or branched alkyl with up to 4 carbon atoms, R$_4$ is selected from a group consisting of hydrogen and straight-chain or branched alkyl with up to 3 carbon atoms, R$_5$ and R$_8$ are the same or different and selected from the group consisting of hydrogen and methyl, R$_6$ is selected from the group consisting of hydrogen and straight-chain or branched alkyl with up to 3 carbon atoms, which is optionally substituted by hydroxy, R$_7$ is selected from the group consisting of straight-chain or branched alkyl with 2 to 6 carbon atoms, which is substituted by a group with the formula —NR$_{23}$R$_{24}$, wherein R$_{23}$ and R$_{24}$ are the same or different and are selected from the group consisting of hydrogen and straight-chain or branched alkyl with up to 4 carbon atoms, which is optionally substituted by hydroxy, or is optionally substituted by phenyl, which in turn is substituted by a group with the formula —SO$_2$—NR$^{25}$R$^{26}$, wherein R$_{25}$ and R$_{26}$ are the same or different and have the meanings given above for R$_9$ and R$_{10}$;

D is selected from a group consisting of hydrogen and from a group with the formula —SO$_2$—NR$^{27}$R$^{28}$;

wherein R$_{27}$ and R$_{28}$ are the same or different and have the meanings given above for R$_9$ and R$_{10}$, and are the same as them or different from them, E is selected from a group consisting of straight-chain or branched alkyl with up to 6 carbon atoms, and their tautomers and salts.

6. The method of claim 4 wherein:

A is selected from a group with the formula

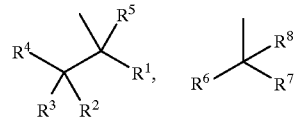

and (CH$_2$)$_a$—CH$_3$, wherein "a" is selected from a group consisting of a number 9, 10, 11, or 12, R$_1$ is selected from a group consisting of a straight-chain or branched alkyl group with 2 to 7 carbon atoms, which is optionally substituted by phenyl, which in turn may be substituted by fluorine, chlorine, bromine, nitro, cyano, straight-chain or branched alkyl with up to 3 carbon atoms, or by a group with the formula —SO$_2$NR$_9$R$_{10}$;

wherein R$_9$ and R$_{10}$ are the same or different, and are selected from a group consisting of hydrogen, phenyl, and straight-chain or branched alkyl with up to 4 carbon atoms, which is optionally substituted by hydroxy, or together with the nitrogen atom they form a morpholinyl, pyrrolidinyl, piperidinyl, or piperazinyl ring, which is also optionally substituted through a free NH function by straight-chain or branched alkyl with up to 3 carbon atoms, which in turn may be substituted by hydroxy, and/or is alkyl optionally substituted by a group with the formula —$NR_{11}R_{12}$ wherein $R_{11}$ and $R_{12}$ have the meanings given above for $R^9$ and $R_{10}$ and are the same as them or different from them, $R_2$ is selected from a group consisting of hydrogen, azido, straight-chain or branched alkyl with up to 3 carbon atoms and a group with the formula —$OR_{13}$, —O—$SO_2R_{14}$, or —$NR_{15}R_{16}$, wherein $R_{13}$ is selected from a group consisting of hydrogen, straight-chain or branched acyl with up to 3 carbon atoms, benzoyl and straight-chain or branched alkyl with up to 3 carbon atoms, which is optionally substituted by carboxy or straight-chain or branched alkoxycarbonyl with up to 3 carbon atoms, or by a group with the formula —CO—$NR_{17}R_{18}$, wherein $R_{17}$ and $R_{18}$ are the same or different and are selected from the group consisting of hydrogen and lower alkyl;

$R_{14}$ is selected from a group consisting of straight-chain or branched alkyl with up to 3 carbon atoms and phenyl, $R_{15}$ and $R_{16}$ are the same or different and are selected from a group consisting of hydrogen, t-butoxycarbonyl, straight-chain or branched alkyl or acyl, each with up to 3 carbon atoms, formyl, benzoyl, and a group with the formula —$SO2R_{19}$, wherein $R_{19}$ has the meaning given above for $R_{14}$ and is the same as or different from it, $R_3$ is selected from a group consisting of hydrogen, or $R_2$ and $R_3$ together form a group with the formula =O or =N—$OR_{20}$, wherein $R_{20}$ is selected from a group consisting of hydrogen and straight-chain or branched alkyl with up to 4 carbon atoms, which is optionally substituted by phenyl or by a group with the formula —$NR_{21}R_{22}$, wherein $R_{21}$ and $R_{22}$ are the same or different and are selected from a group consisting of hydrogen, phenyl, and straight-chain or branched alkyl with up to 3 carbon atoms, $R_4$ is selected from a group consisting of hydrogen and straight-chain or branched alkyl with up to 3 carbon atoms, $R_5$ and $R_8$ are the same or different and are selected from a group consisting of hydrogen and methyl, $R_6$ is selected from a group consisting of hydrogen and straight-chain or branched alkyl with up to 3 carbon atoms, which is optionally substituted by hydroxy, $R_7$ is selected from a group consisting of straight-chain or branched alkyl with 2 to 6 carbon atoms, which is substituted by a group with the formula —$NR_{23}R_{24}$, wherein $R_{23}$ and $R_{24}$ are the same or different and are selected from the groups consisting of hydrogen and a straight-chain or branched alkyl with up to 3 carbon atoms, which is optionally substituted by hydroxy, or is optionally substituted by phenyl, which in turn is substituted by the group with the formula —$SO_2$—$NR_{25}R_{26}$, wherein $R_{25}$ and $R_{26}$ have the meanings given above for $R_9$ and $R_{10}$, D is selected from a group consisting of hydrogen and from a group with the formula —$SO_2$—$NR_{27}R_{28}$, wherein $R_{27}$ and $R_{28}$ are the same or different and have the meanings given above for $R_9$ and $R_{10}$, and are the same as them or different from them, E is selected from a group consisting of straight-chain or branched alkyl with up to 5 carbon atoms, and their tautomers and salts.

7. A method for regulating apoptosis in human cells comprising exposing said cells to a physiologically effective amount of a compound of the formula:

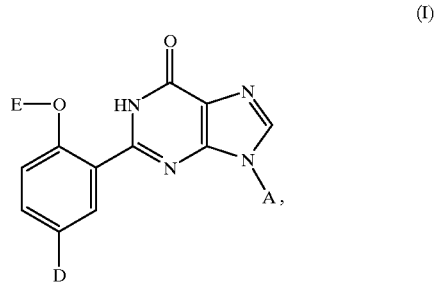

(I)

wherein A is selected from the group consisting of the formula

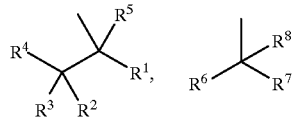

and $(CH_2)_a$—$CH_3$, and "a" is an integer from 9–15;

$R_1$ is selected from the group consisting of a straight-chain or branched alkyl group with 2 to 10 carbon atoms, which is optionally substituted by phenyl, which in turn may be substituted by halogen, nitro, cyano, straight-chain or branched alkyl with up to 6 carbon atoms, and by a group with the formula —$SO_2NR_9R_{10}$;

wherein $R_9$ and $R_{10}$ are the same or different, and are each selected from the group consisting of hydrogen, phenyl, and straight-chain or branched alkyl with up to 6 carbon atoms, which is optionally substituted by hydroxy, or together with the nitrogen atom $R_9$ and $R_{10}$ form a 5- to 6-membered saturated heterocyclic ring with up to 2 other hetero atoms from the group consisting of S, N, and/or O, which is also optionally substituted through a free N function by a straight-chain or branched alkyl with up to 6 carbon atoms, which in turn may be substituted by hydroxy, and/or is alkyl optionally substituted by a group with the formula —$NR_{11}R_{12}$;

wherein $R^2$ is selected from the group consisting of hydrogen, azido, straight-chain or branched alkyl with up to 6 carbon atoms and a group with the formula —$OR_{13}$, —O—$SO_2R_{14}$, and —$NR_{15}R_{16}$;

wherein $R_{13}$ is selected from the group consisting of hydrogen, a hydroxy-protecting group, straight-chain or branched alkyl with up to 6 carbon atoms, benzoyl and straight-chain or branched alkyl with up to 6 carbon atoms, which is optionally substituted by carboxy or straight-chain or branched alkoxycarbonyl with up to 6 carbon atoms, or by a group with the formula —CO—$NR_{17}R_{18}$;

wherein $R_{17}$ and $R_{18}$ are the same or different and are selected from the group consisting of hydrogen and straight-chain or branched alkyl with up to 4 carbon atoms, $R_{14}$ is selected from the group consisting of straight-chain or branched alkyl with up to 4 carbon atoms and phenyl;

$R_{15}$ and $R_{16}$ are the same or different and are selected from a group consisting of hydrogen, an amine-protecting group, straight-chain or branched alkyl or acyl, each with up to 6 carbon atoms, formyl, benzoyl, and a group with the formula —$SO_2R_{19}$, wherein $R_{19}$ has the meaning given above for $R_{14}$ and is the same as or different from it, $R_3$ is selected from a group consisting of hydrogen, or $R^2$ and $R^3$ together form a group of the formula =O or =N—$OR_{20}$;

wherein $R_{20}$ is selected from a group consisting of hydrogen and straight-chain or branched alkyl with up to 6 carbon atoms, which is optionally substituted by phenyl or by a group with the formula —$NR_{21}R_{22}$, wherein $R_{21}$ and $R_{22}$ are the same or different and are selected from a group consisting of hydrogen, phenyl, and straight-chain or branched alkyl with up to 6 carbon atoms, $R_4$ is selected from a group consisting of hydrogen and straight-chain or branched alkyl with up to 4 carbon atoms, $R_5$ and $R_8$ are the same or different and are selected from the group consisting of hydrogen and straight-chain or branched alkyl with up to 3 carbon atoms, $R_6$ is selected from a group consisting of hydrogen and straight-chain or branched alkyl with up to 5 carbon atoms, which is optionally substituted by hydroxy, $R_7$ is selected from the group consisting of straight-chain or branched alkyl with 2 to 8 carbon atoms, which is substituted by a group with the formula —$NR_{23}R_{24}$, wherein $R_{23}$ and $R_{24}$ are the same or different and are selected from the group consisting of hydrogen and straight-chain or branched alkyl with up to 5 carbon atoms, which is optionally substituted by hydroxy, or is optionally substituted by phenyl, which in turn is substituted by the group with the formula —$SO_2$—$NR_{25}R_{26}$;

wherein $R_{25}$ and $R_{26}$ have the meanings given above for $R_9$ and $R_{10}$;

D is selected from a group consisting of hydrogen and a group with the formula —$SO_2$—$NR_{27}R_{28}$;

wherein $R_{27}$ and $R_{28}$ are the same or different and have the meanings given above for $R_9$ and $R_{10}$, and are the same as them or different from them; and E is selected from a group consisting of straight-chain or branched alkyl with up to 8 carbon atoms, and their tautomers and salts.

8. The method of claim 7 wherein A is selected from a group consisting of the formula

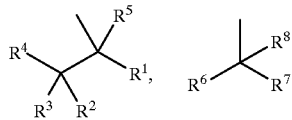

and $(CH_2)_a$—$CH_3$, wherein "a" is an integer from 9–13, $R_1$ is selected from a group consisting of straight-chain or branched alkyl group with 2 to 8 carbon atoms, which is optionally substituted by phenyl, which in turn may be substituted by fluorine, chlorine, bromine, nitro, cyano, straight-chain or branched alkyl with up to 4 carbon atoms, or by a group with the formula —$SO_2N_{11}R_{12}$, wherein $R_9$ and $R_{10}$ are the same or different, and are selected from a group consisting of hydrogen, phenyl, and straight-chain or branched alkyl with up to 5 carbon atoms, which is optionally substituted by hydroxy, or together with the nitrogen atom they form a morpholinyl, pyrrolidinyl, piperidinyl, or piperazinyl ring, which is also optionally substituted through a free NH function by straight-chain or branched alkyl with up to 3 carbon atoms, which in turn may be substituted by hydroxy, and/or is alkyl optionally substituted by a group with the formula —$NR_{11}R_{12}$, wherein $R_{11}R_{12}$ have the meanings given above for $R_9$ and $R_{10}$ and are the same as them or different from them, $R_2$ is selected from a group consisting of hydrogen, azido, straight-chain or branched alkyl with up to 4 carbon atoms and a group with the formula —$OR_{13}$, —O—$SO_2R_{14}$, or —$NR_{15}R_{16}$, wherein $R_{13}$ is selected from a group consisting of hydrogen, benzyl, straight-chain or branched acyl with up to 4 carbon atoms, benzoyl and straight-chain or branched alkyl with up to 4 carbon atoms, which is optionally substituted by carboxy or straight-chain or branched alkoxycarbonyl with up to 4 carbon atoms, or by a group with the formula —CO—$NR_{17}R_{18}$, wherein $R_{17}R_{18}$ are the same or different and are selected from a group consisting of hydrogen and straight-chain or branched alkyl with up to 3 carbon atoms, $R_{14}$ is selected from a group consisting of straight-chain or branched alkyl with up to 3 carbon atoms and phenyl, $R_{15}$ and $R_{16}$ are the same or different and are selected from a group consisting of hydrogen, t-butoxycarbonyl, benzyloxycarbonyl, or straight-chain or branched alkyl and acyl, each with up to 4 carbon atoms, formyl, benzoyl, or a group with the formula —$SO_2R_{19}$, wherein $R_{19}$ has the meaning given above for $R_{14}$ and is the same as or different from it, $R_3$ is selected from a group consisting of hydrogen, or $R_2$ and $R_3$ together form a group of the formula =O or =N—$OR_{20}$, wherein $R_{20}$ is selected from a group consisting of hydrogen and straight-chain or branched alkyl with up to 4 carbon atoms, which is optionally substituted by phenyl or by a group with the formula —$NR_{21}R_{22}$, wherein $R_{21}$ and $R_{22}$ are the same or different and stand for hydrogen, phenyl, and straight-chain or branched alkyl with up to 4 carbon atoms, $R_4$ is selected from a group consisting of hydrogen and straight-chain or branched alkyl with up to 3 carbon atoms, $R_5$ and $R_8$ are the same or different and selected from the group consisting of hydrogen and methyl, $R_6$ is selected from the group consisting of hydrogen and straight-chain or branched alkyl with up to 3 carbon atoms, which is optionally substituted by hydroxy, $R_7$ is selected from the group consisting of straight-chain or branched alkyl with 2 to 6 carbon atoms, which is substituted by a group with the formula —$NR_{23}R_{24}$, wherein $R_{23}$ and $R_{24}$ are the same or different and are selected from the group consisting of hydrogen and straight-chain or branched alkyl with up to 4 carbon atoms, which is optionally substituted by hydroxy, or is optionally substituted by phenyl, which in turn is substituted by a group with the formula —$SO_2$—$NR^{25}R^{26}$, wherein $R_{25}$ and $R_{26}$ are the same or different and have the meanings given above for $R_9$ and $R_{10}$;

D is selected from a group consisting of hydrogen and from a group with the formula —$SO_2$—$NR^{27}R^{28}$;

wherein $R_{27}$ and $R_{28}$ are the same or different and have the meanings given above for $R_9$ and $R_{10}$, and are the same as them or different from them, E is selected from a group consisting of straight-chain or branched alkyl with up to 6 carbon atoms, and their tautomers and salts.

9. The method of claim 7 wherein:

A is selected from a group with the formula

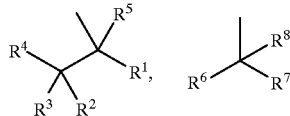

and $(CH_2)_a$—$CH_3$, wherein "a" is selected from a group consisting of a number 9, 10, 11, or 12, $R_1$ is selected from a group consisting of a straight-chain or branched alkyl group with 2 to 7 carbon atoms, which is optionally substituted by phenyl, which in turn may be substituted by fluorine, chlorine, bromine, nitro, cyano, straight-chain or branched alkyl with up to 3 carbon atoms, or by a group with the formula —$SO_2NR_9R_{10}$;

wherein $R_9$ and $R_{10}$ are the same or different, and are selected from a group consisting of hydrogen, phenyl, and straight-chain or branched alkyl with up to 4 carbon atoms, which is optionally substituted by hydroxy, or together with the nitrogen atom they form a molpholinyl, pyrrolidinyl, piperidinyl, or piperazinyl ring, which is also optionally substituted through a free NH function by straight-chain or branched alkyl with up to 3 carbon atoms, which in turn may be substituted by hydroxy, and/or is alkyl optionally substituted by a group with the formula —$NR_{11}R_{12}$ wherein $R_{11}$ and $R_{12}$ have the meanings given above for $R^9$ and $R_{10}$ and are the same as them or different from them, $R_2$ is selected from a group consisting of hydrogen, azido, straight-chain or branched alkyl with up to 3 carbon atoms and a group with the formula —$OR_{13}$, —O—$SO_2R_{14}$, or —$NR_{15}R_{16}$, wherein $R_{13}$ is selected from a group consisting of hydrogen, straight-chain or branched acyl with up to 3 carbon atoms, benzoyl and straight-chain or branched alkyl with up to 3 carbon atoms, which is optionally substituted by carboxy or straight-chain or branched alkoxycarbonyl with up to 3 carbon atoms, or by a group with the formula —CO—$NR_{17}R_{18}$, wherein $R_{17}$ and $R_{18}$ are the same or different and are selected from the group consisting of hydrogen and lower alkyl;

$R_{14}$ is selected from a group consisting of straight-chain or branched alkyl with up to 3 carbon atoms and phenyl, $R_{15}$ and $R_{16}$ are the same or different and are selected from a group consisting of hydrogen, t-butoxycarbonyl, straight-chain or branched alkyl or acyl, each with up to 3 carbon atoms, formyl, benzoyl, and a group with the formula —$SO2R_{19}$, wherein $R_{19}$ has the meaning given above for $R_{14}$ and is the same as or different from it, $R_3$ is selected from a group consisting of hydrogen, or $R_2$ and $R_3$ together form a group with the formula =O or =N—$OR_{20}$, wherein $R_{20}$ is selected from a group consisting of hydrogen and straight-chain or branched alkyl with up to 4 carbon atoms, which is optionally substituted by phenyl or by a group with the formula —$NR_{21}R_{22}$, wherein $R_{21}$ and $R_{22}$ are the same or different and are selected from a group consisting of hydrogen, phenyl, and straight-chain or branched alkyl with up to 3 carbon atoms, $R_4$ is selected from a group consisting of hydrogen and straight-chain or branched alkyl with up to 3 carbon atoms, $R_5$ and $R_8$ are the same or different and are selected from a group consisting of hydrogen and methyl, $R_6$ is selected from a group consisting of hydrogen and straight-chain or branched alkyl with up to 3 carbon atoms, which is optionally substituted by hydroxy, $R_7$ is selected from a group consisting of straight-chain or branched alkyl with 2 to 6 carbon atoms, which is substituted by a group with the formula —$NR_{23}R_{24}$, wherein $R_{23}$ and $R_{24}$ are the same or different and are selected from the groups consisting of hydrogen and a straight-chain or branched alkyl with up to 3 carbon atoms, which is optionally substituted by hydroxy, or is optionally substituted by phenyl, which in turn is substituted by the group with the formula —$SO_2$—$NR_{25}R_{26}$, wherein $R_{25}$ and $R_{26}$ have the meanings given above for $R_9$ and $R_{10}$, D is selected from a group consisting of hydrogen and from a group with the formula —$SO_2$—$NR_{27}R_{28}$, wherein $R_{27}$ and $R_{28}$ are the same or different and have the meanings given above for $R_9$ and $R_{10}$, and are the same as them or different from them, E is selected from a group consisting of straight-chain or branched alkyl with up to 5 carbon atoms, and their tautomers and salts.

* * * * *